US008362319B2

(12) United States Patent
Andre et al.

(10) Patent No.: US 8,362,319 B2
(45) Date of Patent: Jan. 29, 2013

(54) ARABIDOPSIS GENES ENCODING PROTEINS INVOLVED IN SUGAR AND LIPID METABOLISM AND METHODS OF USE

(75) Inventors: Carl Andre, Lansing, MI (US); Alex Cernac, East Lansing, MI (US); Christoph Benning, East Lansing, MI (US); Heiko A. Härtel, Berlin (DE); Volker Mittendorf, Durham, NC (US)

(73) Assignees: BASF Plant Science GmbH (DE); Michigan State University, East Lansing, MI (US)

( * ) Notice: Subject to any disclaimer, the term of this patent is extended or adjusted under 35 U.S.C. 154(b) by 922 days.

(21) Appl. No.: 11/663,250

(22) PCT Filed: Sep. 20, 2005

(86) PCT No.: PCT/US2005/033537
§ 371 (c)(1),
(2), (4) Date: Jun. 23, 2009

(87) PCT Pub. No.: WO2006/034228
PCT Pub. Date: Mar. 30, 2006

(65) Prior Publication Data
US 2009/0265810 A1 Oct. 22, 2009

Related U.S. Application Data

(60) Provisional application No. 60/611,463, filed on Sep. 20, 2004.

(51) Int. Cl.
*C12N 15/82* (2006.01)
*A01H 5/00* (2006.01)
(52) U.S. Cl. .......................................... 800/281; 800/298
(58) Field of Classification Search .................... None
See application file for complete search history.

(56) References Cited

U.S. PATENT DOCUMENTS

| 5,945,585 | A | 8/1999 | Hitz et al. |
| 5,955,650 | A | 9/1999 | Hitz |
| 6,084,164 | A | 7/2000 | Bidney et al. |
| 2004/0019931 | A1 | 1/2004 | Tarczynski et al. |
| 2004/0031072 | A1 | 2/2004 | LaRosa et al. |

FOREIGN PATENT DOCUMENTS

| EP | 1033405 | 9/2000 |
| WO | WO-99/86139 A1 | 11/1999 |
| WO | WO-2004/048535 A2 | 6/2004 |
| WO | WO-2006/069610 A2 | 7/2006 |

OTHER PUBLICATIONS

Doerks et al, TIG 14(6): 248-250, Jun. 1998.*
Bork et al, TIG 12(10): 425-427, Oct. 1996.*
Brenner, S.E., TIG 15(4): 132-133, Apr. 1999.*
Dörmann, P. et al., "Cloning and Expression in *Escherichia coli* of a Novel Thioesterase from *Arabidopsis thaliana* Specific for Long-Chain Acyl-Acyl Carrier Proteins", Archives of Biochemistry and Biophysics, vol. 316, No. 1, 1995, pp. 612-618.
Töpfer, R., et al., "Modification of Plant Lipid Synthesis", Science, vol. 268, 1995, pp. 681-686.
Plaxton, W. C., "The Organization and Regulation of Plant Glycolysis", Annual Rev. Plant Physiol. Plant Mol. Biol. vol. 47, 1996, pp. 185-214.
Kang, F., et al., "Starch and fatty acid synthesis in plastids from developing embryos of oilseed rape (*Brassica napes* L.)", The Plant Journal, vol. 6, No. 6, 1994, pp. 795-805.
"*Arabidopsis thaliana* Full-length cDNA Complete Sequence from clone CSLTPCHSZA04 of Hormone Treated Callus strain col-0 of Arabidopsis thaliana (thale cress)", GenBank Accession No. BX825010, Feb. 6, 2004.
"*Arabidopsis thaliana* AT3g22960/F5N5_15 mRNA, complete cds," Database EMBL Accession No. AY058084, Nov. 5, 2001.
"*Arabidopsis thaliana* AtIg32440/F5D14_7 mRNA, complete cds," Database EMBL Accession No. AY058121, Nov. 5, 2001.
"*Arabidopsis thaliana* clone 109919 mRNA, complete sequence", Database EBI, Accession No. AY084507, Jun. 14, 2002.
Haas, B.J., et al., "Full-Length Messenger RNA Sequences Greatly Improve Genome Annotation", Genome Biology, vol. 3, No. 6, (2002), pp. 1-12.
European Search Report EP10163636, May 9, 2011.
European Search Report EP 10175341, May 6, 2011.
European Search Report EP10175342, May 10, 2011.

* cited by examiner

*Primary Examiner* — Elizabeth McElwain
(74) *Attorney, Agent, or Firm* — Connolly Bove Lodge & Hutz LLP

(57) ABSTRACT

Isolated nucleic acids and polypeptides associated with lipid and sugar metabolism regulation are provided. In particular, lipid metabolism proteins (LMP) and encoding nucleic acids originating from *Arabidopsis thaliana* are provided. The nucleic acids and polypeptides are used in methods of producing transgenic plants and modulating levels of seed storage compounds in a plant. Preferably, the seed storage compounds are lipids, fatty acids, starches, or seed storage proteins.

21 Claims, No Drawings

ARABIDOPSIS GENES ENCODING PROTEINS INVOLVED IN SUGAR AND LIPID METABOLISM AND METHODS OF USE

RELATED APPLICATIONS

This application is a national stage application (under 35 U.S.C. 371) of PCT/US2005/033537 filed Sept. 20, 2005, which claims the benefit of US Provisional Application 60/611,463 filed Sep. 20, 2004.

BACKGROUND OF THE INVENTION

1. Field of the Invention

This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants. The invention further relates to methods of applying these novel plant polypeptides to the identification and stimulation of plant growth and/or to the increase of yield of seed storage compounds.

2. Background Art

The study and genetic manipulation of plants has a long history that began even before the framed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al., 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164), and rapeseed (Töpfer et al., 1995, Science 268:681-686), and non-traditional oilseed plants such as tobacco (Cahoon et al., 1992, Proc. Natl. Acad. Sci. USA 89:11184-11188).

Plant seed oils comprise both neutral and polar lipids (See Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (See Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo et al., 1993, Unusual Fatty Acids in Lipid Metabolism in Plants pp. 91-126, editor TS Moore Jr. CRC Press; Millar et al., 2000, Trends Plant Sci. 5:95-101). Lipids indicated by an asterisk in Table 2 do not normally occur in plant seed oils, but their production in transgenic plant seed oil is of importance in plant biotechnology.

TABLE 1

Plant Lipid Classes

| | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

Common Plant Fatty Acids

| | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid * |
| 20:0 | Arachidic acid |
| 20:1 | Eicosenoic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

Lipids are synthesized from fatty acids and their synthesis may be divided into two parts: the prokaryotic pathway and the eukaryotic pathway (Browse et al., 1986, Biochemical J. 235:25-31; Ohlrogge & Browse, 1995, Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker, 1996, Genetic Engineering ed.:Setlow 18:111-113; Shanklin & Cahoon, 1998, Annu. Rev. Plant Physiol. Plant Mol. Biol. 49:611-641; Frentzen, 1998, Lipids 100:161-166; Millar et al., 2000, Trends Plant Sci. 5:95-101).

Storage lipids in seeds are synthesized from carbohydrate-derived precursors. Plants have a complete glycolytic pathway in the cytosol (Plaxton, 1996, Annu. Rev. Plant Physiol.

Plant Mol. Biol. 47:185-214) and it has been shown that a complete pathway also exists in the plastids of rapeseeds (Kang & Rawsthorne, 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse, 1995, Plant Cell 7:957-970). It is accepted, however, that a large part of the acetyl-CoA is derived from glucose-6-phospate and pyruvate that are imported from the cytoplasm into the plastids. Sucrose is produced in the source organs (leaves, or anywhere that photosynthesis occurs) and is transported to the developing seeds that are also termed sink organs. In the developing seeds, sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Storage compounds such as triacylglycerols (seed oil) serve as carbon and energy reserves, which are used during germination and growth of the young seedling. Seed (vegetable) oil is also an essential component of the human diet and a valuable commodity providing feed stocks for the chemical industry. A mutant of *Arabidopsis* affected in seed storage compound metabolism is wrinkded1 (wri1) (Focks & Benning, 1998, Plant Physiol. 118:91-101). The mutant is characterized by an 80% reduction in seed oil content.

Although the lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (See, e.g., Töpfer et al, 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al., 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al., 1992, Proc. Natl. Acad. Sci. USA 89:11184-11188).

The modification of seed oil content in plants has significant medical, nutritional, and economic ramifications. With regard to the medical ramifications, the long chain fatty acids (C18 and longer) found in many seed oils have been linked to reductions in hypercholesterolemia and other clinical disorders related to coronary heart disease (Brenner, 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid, and acyl-ACP desaturase nucleic acid have been cloned and demonstrated to encode enzymes required for fatty acid synthesis in various plant species. Oleosin nucleic acid sequences from such different species as *Brassica*, soybean, carrot, pine and *Arabidopsis thaliana* also have been cloned and determined to encode proteins associated with the phospbolipid monolayer membrane of oil bodies in those plants.

It has also been determined that two phytohormones, gibberellic acid (GA) and absisic acid (ABA), are involved in overall regulatory processes in seed development (e.g. Ritchie & Gilroy, 1998, Plant Physiol. 116:765-776; Arenas-Huertero et al., 2000, Genes Dev. 14:2085-2096). Both the GA and ABA pathways are affected by okadaic acid, a protein phosphatase inhibitor (Kuo et al., 1996, Plant Cell. 8:259-269). The regulation of protein phosphorylation by kinases and phosphatases is accepted as a universal mechanism of cellular control (Cohen, 1992, Trends Biochem. Sci. 17:408-413). Likewise, the plant hormones ethylene (See, e.g., Zhou et al., 1998, Proc. Natl. Acad. Sci. USA 95:10294-10299; Beaudoin et al., 2000, Plant Cell 2000:1103-1115) and auxin (e.g. Colon-Carmona et al., 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses a large number of nucleic acid sequences from *Arabidopsis thaliana*. These nucleic acid sequences can be used to alter or increase the levels of seed storage compounds such as proteins, sugars, and oils in plants, including transgenic plants, such as rapeseed, canola, linseed, soybean, sunflower, maize, oat, rye, barley, wheat, rice, pepper, tagetes, cotton, oil palm, coconut palm, flax, castor, and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides isolated nucleic acids from *Arabidopsis thaliana* encoding a Lipid Metabolism Protein (LMP), or a portion thereof. These sequences may be used to modify or increase lipids and fatty acids, cofactors and enzymes in microorganisms and plants.

*Arabidopsis* plants are known to produce considerable amounts of fatty acids like linoleic and linolenic acid (See, e.g., Table 2) and for their close similarity in many aspects (gene homology, etc.) to the oil crop plant *Brassica*. Therefore, nucleic acid molecules originating from a plant like *Arabidopsis thaliana* are especially suited to modify the lipid and fatty acid metabolism in a host, especially in microorganisms and plants. Furthermore, nucleic acids from the plant *Arabidopsis thaliana* can be used to identify those DNA sequences and enzymes in other species, which are useful to modify the biosynthesis of precursor molecules of fatty acids in the respective organisms.

The present invention further provides an isolated nucleic acid comprising a fragment of at least 15 nucleotides of a nucleic acid from a plant (*Arabidopsis thaliana*) encoding a Lipid Metabolism Protein (LMP), or a portion thereof.

Also provided by the present invention are polypeptides encoded by the nucleic acids, heterologous polypeptides comprising polypeptides encoded by the nucleic acids, and antibodies to those polypeptides.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising an LMP nucleic acid, and generating a plant with a modified level of the seed storage compound from the plant cell. In one embodiment, the plant is a high oil producing species as described in Kinney et al. (1994, Current Opin. in Biotech. 5:144-151), Töpfer et al. (1995, Science 268:681-686), and Oil Crops of the World-Their Breeding and Utilization (1989, eds. Röbbelen, Downey, and Ashri). In a preferred embodiment, the plant is an oil producing species selected from the group consisting of rapeseed, canola, linseed, soybean, sunflower, maize, oat, rye, barley, wheat, rice, pepper, tagetes, cotton, oil palm, coconut palm, flax, castor and peanut, for example.

According to the present invention, the compositions and methods described herein can be used to increase or decrease the level of an LMP in a transgenic plant comprising increasing or decreasing the expression of an LMP nucleic acid in the plant. Increased or decreased expression of the LMP nucleic acid can be achieved through transgenic expression, cosuppression, antisense inhibition, or in vivo mutagenesis of the LMP nucleic acid. The present invention also can be used to increase or decrease the level of a lipid in a seed oil, to increase or decrease the level of a fatty acid in a seed oil, or to increase or decrease the level of a starch in a seed or plant.

The present invention provides transgenic plants having modified levels of seed storage compounds, and in particular, modified levels of a lipid, a fatty acid, or a sugar. Also included herein is a seed produced by a transgenic plant transformed by an LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing an LMP nucleic acid from *Arabidopsis thaliana* in the transgenic plant, wherein the transgenic plant is *Arabidopsis thaliana* or a species different from *Arabidopsis thaliana*. Also included herein are compositions and methods of the modification of the efficiency of production of a seed storage compound.

The present invention provides novel isolated LMP nucleic acids and isolated LMP amino acid sequences from *Arabidopsis thaliana* as well as active fragments, analogs and orthologs thereof. The polynucleotides and polypeptides of the present invention, including agonists and/or fragments thereof may have uses that include modulating plant growth, and potentially plant yield, preferably increasing plant growth under adverse conditions (drought, cold, light, UV). In addition, antagonists of the present invention may have uses that include modulating plant growth and/or yield, through preferably increasing plant growth and yield. In yet another embodiment, overexpression polypeptides of the present invention using a constitutive promoter (e.g., 35S, or other promoters) may be useful for increasing plant yield under stress conditions (drought, light, cold, UV) by modulating light utilization efficiency.

The present invention also provides methods for producing such aforementioned transgenic plants.

The present invention further provides seeds and seed oils from such aforementioned transgenic plants.

These and other features and advantages of the present invention will become apparent after a review of the following detailed description of the disclosed embodiments and the appended claims.

DETAILED DESCRIPTION OF THE INVENTION

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purposes of this invention, as embodied and described herein, this invention, in one aspect, provides an isolated nucleic acid from a plant (*Arabidopsis thaliana*) encoding a Lipid Metabolism Protein (LMP), or a portion thereof.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an *Arabidopsis thaliana* cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence as shown in the Appendix, or a portion thereof, can be isolated using standard molecular biology techniques and the sequence information provided herein. For example, an *Arabidopsis thaliana* LMP cDNA can be isolated from an *Arabidopsis thaliana* library using all or portion of one of the sequences as shown in the Appendix as a hybridization probe and standard hybridization techniques (e.g., as described in Sambrook et al. 1989, Molecular Cloning: A Laboratory Manual. 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences as shown in the Appendix can be isolated by the polymerase chain reaction using oligonucleotide primers designed based upon this sequence (e.g., a nucleic acid molecule encompassing all or a portion of one of the sequences as shown in the Appendix can be isolated by the polymerase chain reaction using oligonucleotide primers designed based upon this same sequence as shown in the Appendix). For example, mRNA can be isolated from plant cells (e.g., by the guanidinium-thiocyanate extraction procedure of Chirgwin et al., 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences as shown in the Appendix. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an LMP nucleotide sequence can be prepared by standard synthetic techniques, e.g., using an automated DNA synthesizer.

In a preferred embodiment, an isolated nucleic acid of the invention comprises one of the nucleotide sequences as shown in the Appendix. The sequences as shown in the Appendix correspond to the *Arabidopsis thaliana* LMP cDNAs of the invention. These cDNAs comprise sequences encoding LMPs (i.e., the "coding region", as shown in the Appendix), as well as 5' untranslated sequences and 3' untranslated sequences. Alternatively, the nucleic acid molecules can comprise only the coding region of any of the sequences as shown in the Appendix or can contain whole genomic fragments isolated from genomic DNA.

For the purposes of this application, it will be understood that each of the sequences set forth in the Appendix has an identifying entry number (e.g., pk309). Each of these sequences may generally comprise three parts: a 5' upstream region, a coding region, and a downstream region. A coding region of these sequences is indicated as "ORF position" (Table 3).

In another preferred embodiment, an isolated nucleic acid molecule of the invention comprises a nucleic acid molecule, which is a complement of one of the nucleotide sequences shown as shown in the Appendix, or a portion thereof. A nucleic acid molecule which is complementary to one of the nucleotide sequences shown as shown in the Appendix is one which is sufficiently complementary to one of the nucleotide sequences shown as shown in the Appendix such that it can hybridize to one of the nucleotide sequences shown as shown in the Appendix, thereby forming a stable duplex.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown as shown in the Appendix, or a portion thereof. In an additional preferred embodiment, an isolated nucleic acid molecule of the invention comprises a nucleotide sequence which hybridizes, e.g., hybridizes under stringent conditions, to one of the nucleotide sequences shown as shown in the Appendix, or a portion thereof. These hybridization conditions include washing with a solution having a salt concentration of about 0.02 M at pH 7 at about 60° C.

Moreover, the nucleic acid molecule of the invention can comprise only a portion of the coding region of one of the sequences shown in the Appendix, for example, a fragment, which can be used as a probe or primer or a fragment encoding a biologically active portion of an LMP. The nucleotide sequences determined from the cloning of the LMP genes from *Arabidopsis thaliana* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in the Appendix, an anti-sense sequence of one of the sequences set forth in the Appendix, or naturally occurring mutants thereof. Primers based on a nucleotide sequence as shown in the Appendix can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an LMP, such as by measuring a level of an LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence as shown in the Appendix such that the protein or portion thereof maintains the same or a similar function as the wild-type protein. As used herein, the language "sufficiently homologous" refers to proteins or portions thereof which have amino acid sequences which include a minimum number of identical or equivalent (e.g., an amino acid residue which has a similar side chain as an amino acid residue in one of the polypeptides encoded by the ORF of a sequence shown in the Appendix) amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. Regulatory proteins, such as DNA binding proteins, transcription factors, kinases, phosphatases, or protein members of metabolic pathways such as the lipid, starch and protein biosynthetic pathways, or membrane transport systems, may play a role in the biosynthesis of seed storage compounds. Examples of such activities are described herein (see putative annotations in Table 3). Examples of LMP-encoding nucleic acid sequences are set forth in the Appendix.

As altered or increased sugar and/or fatty acid production is a general trait wished to be inherited into a wide variety of plants like maize, wheat, rye, oat, triticale, rice, barley, soybean, peanut, cotton, rapeseed, canola, manihot, pepper, sunflower, sugarbeet, tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops, these crop plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of an LMP" is intended to include a portion, e.g., a domain/motif, of an LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether an LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14.

Biologically active portions of an LMP include peptides comprising amino acid sequences derived from the amino acid sequence of an LMP (e.g., an amino acid sequence encoded by a nucleic acid as shown in the Appendix or the amino acid sequence of a protein homologous to an LMP, which include fewer amino acids than a full length LMP or the full length protein which is homologous to an LMP) and exhibit at least one activity of an LMP. Typically, biologically active portions (peptides, e.g., peptides which are, for example, 5, 10, 15, 20, 30, 35, 36, 37, 38, 39, 40, 50, 100, or more amino acids in length) comprise a domain or motif with at least one activity of an LMP. Moreover, other biologically active portions, in which other regions of the protein are deleted, can be prepared by recombinant techniques and evaluated for one or more of the activities described herein. Preferably, the biologically active portions of an LMP include one or more selected domains/motifs or portions thereof having biological activity.

Additional nucleic acid fragments encoding biologically active portions of an LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the nucleotide sequences shown as shown in the Appendix (and portions thereof) due to degeneracy of the genetic code and thus encode the same LMP as that encoded by the nucleotide sequences shown as shown in the Appendix. In a further embodiment, the nucleic acid molecule of the invention encodes a full length protein which is substantially homologous to an amino acid sequence of a polypeptide encoded by an open reading frame shown as shown in the Appendix. In one embodiment, the full-length nucleic acid or protein or fragment of the nucleic acid or protein is from *Arabidopsis thaliana*.

In addition to the *Arabidopsis thaliana* LMP nucleotide sequences shown as shown in the Appendix, it will be appreciated by those skilled in the art that DNA sequence polymorphisms that lead to changes in the amino acid sequences of LMPs may exist within a population (e.g., the *Arabidopsis thaliana* population). Such genetic polymorphism in the LMP gene may exist among individuals within a population due to natural variation. As used herein, the terms "gene" and "recombinant gene" refer to nucleic acid molecules comprising an open reading frame encoding an LMP, preferably a *Arabidopsis thaliana* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana* orthologs of the *Arabidopsis thaliana* LMP cDNA of the invention can be isolated based on their homology to *Arabidopsis thaliana* LMP nucleic acid disclosed herein using the *Arabidopsis thaliana* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a nucleotide sequence as shown in the Appendix. In other embodiments, the nucleic acid is at least 30, 50, 100, 250, or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y., 1989, 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Another preferred example of stringent hybridization conditions is hybridization in a 6×SSC solution at 65° C. Preferably, an isolated nucleic acid molecule of the invention that hybridizes under stringent conditions to a sequence as shown in the Appendix corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Arabidopsis thaliana* LMP.

In addition to naturally-occurring variants of the LMP sequence that may exist in the population, the skilled artisan will further appreciate that changes can be introduced by mutation into a nucleotide sequence as shown in the Appendix, thereby leading to changes in the amino acid sequence of the encoded LMP, without altering the functional ability of the LMP. For example, nucleotide substitutions leading to amino acid substitutions at "non-essential" amino acid residues can be made in a sequence as shown in the Appendix. A "non-essential" amino acid residue is a residue that can be altered from the wild-type sequence of one of the LMPs (polypeptides encoded by any of the sequences as shown in the Appendix) without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment the isolated nucleic acid molecule comprises a nucleotide sequence encoding a protein, wherein the protein comprises an amino acid sequence at least about 50% homologous to an amino acid sequence encoded by a nucleic acid as shown in the Appendix and is capable of participation in the metabolism of compounds necessary for the production of seed storage compounds in *Arabidopsis thaliana*, or cellular membranes, or has one or more activities set forth in Table 3. Preferably, the protein encoded by the nucleic acid molecule is at least about 50-60% homologous to one of the sequences encoded by a nucleic acid as shown in the Appendix, more preferably at least about 60-70% homologous to one of the sequences encoded by a nucleic acid as shown in the Appendix, even more preferably at least about 70-80%, 80-90%, 90-95% homologous to one of the sequences encoded by a nucleic acid as shown in the Appendix, and most preferably at least about 96%, 97%, 98%, or 99% homologous to one of the sequences encoded by a nucleic acid as shown in the Appendix.

To determine the percent homology of two amino acid sequences (e.g., one of the sequences encoded by a nucleic acid as shown in the Appendix and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by a nucleic acid as shown in the Appendix) is occupied by the same amino acid residue or nucleotide as the corresponding position in the other sequence (e.g., a mutant form of the sequence selected from the polypeptide encoded by a nucleic acid as shown in the Appendix), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding an LMP homologous to a protein sequence encoded by a nucleic acid as shown in the Appendix can be created by introducing one or more nucleotide substitutions, additions or deletions into a nucleotide sequence as shown in the Appendix such that one or more amino acid substitutions, additions or deletions are introduced into the encoded protein. Mutations can be introduced into one of the sequences as shown in the Appendix by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidin e), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an LMP is preferably replaced with another amino acid residue from the same side chain family. Alternatively, in another embodiment, mutations can be introduced randomly along all or part of an LMP coding sequence, such as by saturation mutagenesis, and the resultant mutants can be screened for an LMP activity described herein to identify mutants that retain LMP activity. Following mutagenesis of one of the sequences as shown in the Appendix, the encoded protein can be expressed recombinantly, and the activity of the protein can be determined using, for example, assays described herein (See Examples 11-13).

LMPs are preferably produced by recombinant DNA techniques. For example, a nucleic acid molecule encoding the protein is cloned into an expression vector (as described above), the expression vector is introduced into a host cell (as described herein) and the LMP is expressed in the host cell. The LMP can then be isolated from the cells by an appropriate purification scheme using standard protein purification techniques. Alternative to recombinant expression, an LMP or peptide thereof can be synthesized chemically using standard peptide synthesis techniques. Moreover, native LMP can be isolated from cells, for example using an anti-LMP antibody, which can be produced by standard techniques utilizing an LMP or fragment thereof of this invention.

The invention also provides LMP chimeric or fusion proteins. As used herein, an LMP "chimeric protein" or "fusion protein" comprises an LMP polypeptide operatively linked to a non-LMP polypeptide. An "LMP polypeptide" or "LMP protein" refers to a polypeptide having an amino acid sequence corresponding to an LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. With respect to the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is an LMP containing a heterologous signal sequence at its N-terminus. In certain host cells (e.g., mammalian host cells), expression and/or secretion of an LMP can be increased through use of a heterologous signal sequence.

Preferably, an LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (See, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding an LMP. The term "coding region" refers to the region of the nucleotide sequence comprising codons that are translated into amino acid residues (e.g., the entire coding region of pk309 comprises nucleotides 214 to 1299). In another embodiment, the antisense nucleic acid molecule is antisense to a "noncoding region" of the coding strand of a nucleotide sequence encoding LMP. The term "noncoding region" refers to 5' and 3' sequences which flank the coding region, that are not translated into amino acids (i.e., also referred to as 5' and 3' untranslated regions).

Given the coding strand sequences encoding LMP disclosed herein (e.g., the sequences as shown in the Appendix), antisense nucleic acids of the invention can be designed according to the rules of Watson and Crick base pairing. The antisense nucleic acid molecule can be complementary to the entire coding region of LMP mRNA, but more preferably is an oligonucleotide. which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45, or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methyl-aminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-xyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding an LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual units, the strands run parallel to each other (Gaultier et al., 1987, Nucleic Acids Res. 15:6625-6641). The antisense nucleic acid molecule can also comprise a 2'-o-methyl-ribonucleotide (Inoue et al., 1987, Nucleic Acids Res.

15:6131-6148) or a chimeric RNA-DNA analogue (Inoue et al., 1987, FEBS Lett. 215:327-330).

In still another embodiment, an antisense nucleic acid of the invention is a ribozyme. Ribozymes are catalytic RNA molecules with ribonuclease activity, which are capable of cleaving a single-stranded nucleic acid, such as an mRNA, to which they have a complementary region. Thus, ribozymes (e.g., hammerhead ribozymes (described in Haselhoff & Gerlach, 1988, Nature 334:585-591)) can be used to catalytically cleave LMP mRNA transcripts to thereby inhibit translation of LMP mRNA. A ribozyme having specificity for an LMP-encoding nucleic acid can be designed based upon the nucleotide sequence of an LMP cDNA disclosed herein (i.e., any of the sequences as shown in the Appendix) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an LMP-encoding mRNA (See, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (See, e.g., Bartel & Szostak, 1993, Science 261:1411-1418).

Alternatively, LMP gene expression can be inhibited by targeting nucleotide sequences complementary to the regulatory region of an LMP nucleotide sequence (e.g., an LMP promoter and/or enhancer) to form triple helical structures that prevent transcription of an LMP gene in target cells (See generally, Helene, 1991, Anticancer Drug Des. 6:569-84; Helene et al., 1992, Ann. N.Y. Acad. Sci. 660:27-36; and Maher, 1992, Bioassays 14:807-15).

Another aspect of the invention pertains to vectors, preferably expression vectors, containing a nucleic acid encoding an LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990), or see Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those that direct constitutive expression of a nucleotide sequence in many types of host cell and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovins expression vectors), yeast and other fungal cells (See Romanos et al., 1992, Foreign gene expression in yeast: a review, Yeast 8:423-488; van den Hondel et al., 1991, Heterologous gene expression in filamentous fungi, in: More Gene Manipulations in Fungi, Bennet & Lasure, eds., p. 396-428: Academic Press: an Diego; and van den Hondel & Punt, 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1:239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia*, especially of the genus *Stylonychia lemnae* with vectors following a transformation method as described in WO 98/01572, and multicellular plant cells (See Schmidt & Willmitzer, 1988, Plant Cell Rep.:583-586); Plant Molecular Biology and Biotechnology, C Press, Boca Raton, Fla., chapter 6/7, S. 71-119 (1993); White, Jenes et al., Techniques for Gene Transfer, in: Transgenic Plants, Vol. 1, Engineering and Utilization, eds.: Kung and Wu, Academic Press 1993, 128-43; Potrykus, 1991, Annu. Rev. Plant Physiol. Plant Mol. Biol. 42:205-225 (and references cited therein), or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith & Johnson 1988, Gene 67:3140), pMAL (New England Biolabs, Beverly, Mass.) and pRITS (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al., 1988, Gene 69:301-315) and pET 11d (Studier et al., 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21DE3) or HMS174(DE3) from a resident prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, 1990, Gene Expression Technology:Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al., 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al., 1987, Embo J. 6:229-234), pMFa (Kuijan & Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt, 1991, "Gene transfer systems and vector development for filamentous fungi," in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al., 1983, Mol. Cell. Biol. 3:2156-2165) and the pVL series (Lucklow & Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells see chapters 16 and 17 of Sambrook, Fritsh and Maniatis, Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the LMPs of the invention may be expressed in uni-cellular plant cells (such as algae; see Falciatore et al., 1999, Marine Biotechnology 1:239-251, and references therein) and plant cells from higher plants (e.g., the spermatophytes, such as crop plants). Examples of plant expression vectors include those detailed in: Becker et al., 1992, Plant Mol. Biol. 20:1195-1197) and Bevan, 1984, Nucleic Acids Res. 12:8711-8721; Vectors for Gene Transfer in Higher Plants; in: Transgenic Plants, Vol. 1, Engineering and Utilization, eds.: Kung und R. Wu, Academic Press, 1993, S. 15-38).

A plant expression cassette preferably contains regulatory sequences capable to drive gene expression in plant cells and which are operatively linked so that each sequence can fulfill its function such as termination of transcription, including polyadenylation signals. Preferred polyadenylation signals are those originating from *Agrobacterium tumefaciens* t-DNA such as the gene 3 known as octopine synthase of the Ti-plasmid pTiACH$_5$ (Gielen et al., 1984, EMBO J. 3:835) or functional equivalents thereof but also all other terminators functionally active in plants are suitable.

As plant gene expression is very often not limited on transcriptional levels a plant expression cassette preferably contains other operatively linked sequences like translational enhancers such as the overdrive-sequence containing the 5'-untranslated leader sequence from tobacco mosaic virus enhancing the protein per RNA ratio (Gallie et al., 1987, Nucleic Acids Res. 15:8693-8711).

Plant gene expression has to be operatively linked to an appropriate promoter conferring gene expression in a timely, cell, or tissue specific manner. Preferred are promoters driving constitutive expression (Benfey et al., 1989, EMBO J. 8:2195-2202) like those derived from plant viruses like the 35S CAMV (Franck et al., 1980, Cell 21:285-294), the 19S CaMV (See also U.S. Pat. No. 5,352,605 and WO 84/02913), or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al., 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce-4-promoter from *Brassica* (WO 91/13980) or the legumin B4 promoter (LeB4; Baeumlein et al., 1992, Plant J. 2:233-239) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the Sorghum kasirin-gene, and the rye secalin gene).

Plant gene expression can also be facilitated via an inducible promoter (For a review, see Gatz, 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (For a review, see Kermode, 1996, Crit. Rev. Plant Sci. 15:285423 and references cited therein) such as the vacuole, the nucleus, all types of plastids like amyloplasts, chloroplasts, chromoplasts, the extracellular space, mitochondria, the endoplasmic reticulum, oil bodies, peroxisomes, and other compartments of plant cells. Also especially suited are promoters that confer plastid-specific gene expression, as plastids are the compartment where precursors and some end products of lipid biosynthesis are synthesized. Suitable promoters such as the viral RNA polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an LMP can be expressed in bacterial cells, insect cells, fungal cells, mammalian cells (such as Chinese hamster ovary cells (CHO) or COS cells), algae, ciliates or plant cells. Other suitable host cells are known to those skilled in the art.

Vector DNA can be introduced into prokaryotic or eukaryotic cells via conventional transformation or transfection techniques. As used herein, the terms "transformation," "transfection," "conjugation," and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, Molecular Cloning. A Laboratory Manual. 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin, kanamycin, and methotrexate, or in plants that confer resistance towards an herbicide such as glyphosate or glufosinate. A nucleic acid encoding a selectable marker can be introduced into a host cell on the same vector as that encoding an LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of an LMP gene into which a deletion, addition or substitution has been introduced to thereby alter, e.g., functionally disrupt, the LMP gene. Preferably, this LMP gene is an *Arabidopsis thaliana* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al., 1999, Nucleic Acids Res. 27:1323-1330 and Kmiec, 1999, American Scientist 87:240-247). Homologous recombination procedures in *Arabidopsis thaliana* and other crops are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous IMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (See e.g., Thomas & Capecchi, 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems that allow for regulated expression of the introduced gene. For example, inclusion of an LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) an LMP. Accordingly, the invention further provides methods for producing LMPs using the host cells of the invention. In one embodiment, the method comprises culturing a host cell of the invention (into which a recombinant expression vector encoding an LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals that are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana* LMP in other plants than *Arabidopsis thaliana* or microorganisms, algae, or fungi.

An isolated LMP or a portion thereof of the invention can participate in the metabolism of compounds necessary for the production of seed storage compounds in *Arabidopsis thaliana* or another plant, or of cellular membranes, or has one or more of the activities set forth in Table 3. In preferred embodiments, the protein or portion thereof comprises an amino acid sequence which is sufficiently homologous to an amino acid sequence encoded by a nucleic acid as shown in the Appendix such that the protein or portion thereof maintains the ability to participate in the metabolism of compounds necessary for the construction of cellular membranes in *Arabidopsis thaliana*, or in the transport of molecules across these membranes. The portion of the protein is preferably a biologically active portion as described herein. In another preferred embodiment, an LMP of the invention has an amino acid sequence encoded by a nucleic acid as shown in the Appendix. In yet another preferred embodiment, the LMP has an amino acid sequence which is encoded by a nucleotide sequence that hybridizes, e.g., hybridizes under stringent conditions, to a nucleotide sequence as shown in the Appendix. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99%, or more homologous to one of the amino acid sequences encoded by a nucleic acid as shown in the Appendix. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence as shown in the Appendix, and which can participate in the metabolism of compounds necessary for the construction of cellular membranes in *Arabidopsis thaliana*, or in the transport of molecules across these membranes, or which has one or more of the activities set forth in Table 3.

In other embodiments, the LMP is substantially homologous to an amino acid sequence encoded by a nucleic acid as shown in the Appendix and retains the functional activity of the protein of one of the sequences encoded by a nucleic acid as shown in the Appendix yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99%, or more homologous to an entire amino acid sequence and which has at least one of the LMP activities described herein. In another embodiment, the invention pertains to a full *Arabidopsis thaliana* protein, which is substantially homologous to an entire amino acid sequence encoded by a nucleic acid as shown in the Appendix.

Dominant negative mutations or trans-dominant suppression can be used to reduce the activity of an LMP in transgenics seeds in order to change the levels of seed storage compounds. To achieve this a mutation that abolishes the activity of the LMP is created and the inactive non-functional LMP gene is overexpressed in the transgenic plant The inactive transdominant LMP protein competes with the active endogenous LMP protein for substrate or interactions with other proteins and dilutes out the activity of the active LMP. In this way the biological activity of the LMP is reduced without actually modifying the expression of the endogenous LMP gene. This strategy was used by Pontier et al to modulate the activity of plant transcription factors (Pontier et al., Plant J 2001, 27(6):529-38).

Homologues of the LMP can be generated by mutagenesis, e.g., discrete point mutation or truncation of the LMP. As used herein, the term "homologue" refers to a variant form of the LMP that acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP by, for example, competitively binding to a downstream or upstream member of the cell membrane component metabolic cascade which includes the LMP, or by binding to an LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods that can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acids Res. 11:477).

In addition, libraries of fragments of the LMP coding sequences can be used to generate a variegated population of LMP fragments for screening and subsequent selection of homologues of an LMP. In one embodiment, a library of coding sequence fragments can be generated by treating a double stranded PCR fragment of an LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify LMP homologues (Arkin & Yourvan, 1992, Proc. Natl. Acad. Sci. USA 89:7811-7815; Delgrave et al., 1993, Protein Engineering 6:327-331). In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Arabidopsis thaliana* and related organisms; mapping of genomes of organisms related to *Arabidopsis thaliana*; identification and localization of *Arabidopsis thaliana* sequences of interest; evolutionary studies; determination of LMP regions required for function; modulation of an LMP activity, modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as canola or soybean, which require light to drive photosynthesis and growth. Plants like *Arabidopsis thaliana* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana* or a close relative thereof. Also, they may be used to identify the presence of *Arabidopsis thaliana* or a relative thereof in a mixed population of microorganisms. The invention provides the nucleic acid sequences of a number of *Arabidopsis thaliana* genes; by probing the extracted genomic DNA of a culture of a unique or mixed population of microorganisms under stringent conditions with a probe spanning a region of an *Arabidopsis thaliana* gene, which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana* proteins. For example, to identify the region of the genome to which a particular *Arabidopsis thaliana* DNA-binding protein binds, the *Arabidopsis thaliana* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of an LMP of the invention may directly affect the accumulation and/or composition of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where overexpression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al., 2000, Plant J. 24:383-396) and the lipid composition in leaves and roots (Härtel et al., 2000, Proc. Natl. Acad. Sci. USA 97:10649-10654). Likewise, the activity of the plant ACCase has been demonstrated to be regulated by phosphorylation (Savage & Ohlrogge, 1999, Plant J. 18:521-527), and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (See, e.g., Müller et al., 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al., 2001, Plant J. 25:295-303). For more examples, see also the section 'Background of the Invention.'

The present invention also provides antibodies, which specifically binds to an LMP-polypeptide, or a portion thereof, as encoded by a nucleic acid disclosed herein or as described herein. Antibodies can be made by many well-known methods (See, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (See, for example, Kelly et al., 1992, BioTechnology 10:163-167; Bebbington et al., 1992, BioTechnology 10:169-175).

The phrase "selectively binds" with the polypeptide refers to a binding reaction, which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes
a) General Cloning Processes:
Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics," Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg), and Sigma (Deisenhofen). Solutions were prepared using purified, pyrogen-free water, designated as H2O in the following text, from a Millie water system water purification plant (Millipore, Eschborn). Restriction endonucleases, DNA-modifying enzymes and molecular biology kits were obtained from the companies AGS (Heidelberg), Amersham (Braunschweig), Biometra (Gottingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material and Growth

*Arabidopsis thaliana* Plants

For this study, root material, leaves, siliques and seeds of wild-type and mutant plants of *Arabidopsis thaliana* were used. The wri1 mutation was isolated from an ethyl methanesulfonate-mutagenized population of the Columbia ecotype as described (Benning et al. 1998, Plant Physiol 118:91-101). Wild type and wri1 *Arabidopsis* seeds were preincubated for three days in the dark at 4° C. before placing them into an incubator (AR-75, Percival Scientific, Boone, Iowa) at a photon flux density of 60-80 $\mu mol\, m^{-2}\, s^{-1}$ and a light period of 16 hours (22° C.), and a dark period of 8 hours (18° C.). All plants were started on half-strength MS medium (Murashige & Skoog, 1962, Plant Physiol. 15:473-497), pH 6.2, 2% sucrose and 1.2% agar. Seeds were sterilized for 20 minutes in 20% bleach 0.5% triton X100 and rinsed 6 times with excess sterile water. Plants were either grown as described above or on soil under standard conditions as described in Focks & Benning (1998, Plant Physiol 118:91-101).

In other series of experiments, siliques of individual ecotypes of *Arabidopsis thaliana* and of selected *Arabidopsis* mutants were used. Seeds were obtained from the *Arabidopsis* stock center.

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The bomogenate obtained was distributed into two Eppendorf vessels (2 ml) and extracted twice by shaking with the same volume of chloroform/isoamyl alcohol (24:1). For phase separation, centrifugation was carried out at 8000 g at room temperature for 15 minutes in each case. The DNA was then precipitated at –70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at –70° C. for 30 minutes using twice the volume of absolute ethanol. After a washing step with 70% ethanol, the DNA was dried and subsequently taken up in 50 μL of H2O+RNAse (50 mg/ml final concentration). The DNA was dissolved overnight at 4° C. and the RNAse digestion was subsequently carried out at 37° C. for 1 h. Storage of the DNA took place at 4° C.

Example 3

Isolation of Total RNA and poly-(A)+ RNA from Plants

For the investigation of transcripts, both total RNA and poly-(A)+ RNA were isolated. RNA is isolated from siliques of *Arabidopsis* plants according to the following procedure:

RNA preparation from *Arabidopsis* seeds—"hot" extraction:

1. Buffers, enzymes, and solutions

2M KCl
Proteinase K
Phenol (for RNA)
Chloroform:Isoamylalcohol (Phenol:choloroform 1:1; pH adjusted for RNA)
4 M LiCl, DEPC-treated
DEPC-treated water
3M NaOAc, pH 5, DEPC-treated
Isopropanol
70% ethanol (made up with DEPC-treated water)
Resuspension buffer: 0.5% SDS, 10 mM Tris pH 7.5, 1 mM EDTA made up with DEPC-treated water as this solution can not be DEPC-treated
Extraction Buffer:
  0.2M Na Borate
  30 mM EDTA
  30 mM EGTA
  1% SDS (250 μl of 10% SDS-solution for 2.5 ml buffer)
  1% Deoxycholate (25 mg for 2.5 ml buffer)
  2% PVPP (insoluble—50 mg for 2.5 ml buffer)
  2% PVP 40K (50 mg for 2.5 ml buffer)
  10 mM DTT
  100 mM β-Mercaptoethanol (fresh, handle under fume hood—use 35 μl of 14.3 M solution for 5 ml buffer)

2. Extraction

The extraction buffer is heated up to 80° C. Tissues are ground in liquid nitrogen-cooled mortar and transferred tissue powder to 1.5 ml tubes. Tissue should be kept frozen until buffer is added, therefore, the samples are transferred with a pre-cooled spatula and the tube is kept in liquid nitrogen at all times. Then 350 μl preheated extraction buffer is added (here, for 100 mg tissue, buffer volume can be as much as 500 μl for bigger samples) to tube. The tube is vortexed, heated to 80° C. for ~1 minute, and then kept on ice. Samples are vortexed and ground additionally with electric mortar.

3. Digestion

Proteinase K (0.15 mg/100 mg tissue) is added. Then the samples are vortexed and kept at 37° C. for one hour.

First Purification

First, 27 μl 2 M KCl is added, and then samples are chilled on ice for 10 minutes. The samples are centrifuged at 12,000 rpm for 10 minutes at room temperature, and then the supernatant is transferred to fresh, RNAase-free tubes. One phenol extraction is performed, followed by a chloroform:isoamyl alcohol extraction. One volume isopropanol is added to supernatant, and the mixture is chilled on ice for 10 minutes. RNA is pelleted by centrifugation (7000 rpm for 10 minutes at room temperature). The RNA pellets are dissolved in 1 ml 4M LiCl by 10 to 15 minutes vortexing. RNA is pelleted by 5 minutes centrifugation.

Second Purification

The pellets are resuspended in 500 µl Resuspension buffer. Then, 500 µl phenol is added, and the samples are vortexed. Then, 250 µl chloroform:isoamylalcohol is added, the samples are vortexed and then centrifuged for 5 minutes. The supernatant is transferred to a fresh tube, and the choloform:isoamylalcohol extraction is repeated until the interface is clear. The supernatant is transferred to a fresh tube, and 1/10 vol 3 M NaOAc, pH 5 and 600 µl isopropanol are added. The samples are kept at −20 C for 20 minutes or longer. RNA is pelleted by 10 minutes centrifugation, and the pellets are washed once with 70% ethanol. All remaining alcohol is removed before resolving the pellets with 15 to 20 µL DEPC-water. The quantity and quality of RNA are determined by measuring the absorbance of a 1:200 dilution at 260 and 280 nm. 40 µg RNA/ml=1 OD260

RNA from wild-type and the wri1 mutant of *Arabidopsis* is isolated as described (Hosein, 2001, Plant Mol. Biol. Rep. 19, 65a-65e; Ruuska et al., 2002, Plant Cell 14, 1191-1206). The mRNA is prepared from total RNA, using the Amersham Pharmacia Biotech mRNA purification kit, which utilizes oligo(d)-cellulose columns. Poly-A)+ RNA is isolated using Dyna Beads® (Dynal, Oslo, Norway) following the instructions of the manufacturer's protocol. After determination of the concentration of the RNA or of the poly(A)+ RNA, the RNA is precipitated by addition of 1/10 volumes of 3 M sodium acetate pH 4.6 and 2 volumes of ethanol and stored at −70° C.

Example 4 cDNA Library Construction

For cDNA library construction, first strand synthesis was achieved using Murine Leukemia Virus reverse transcriptase (Roche, Mannheim, Germany) and oligo-d(T)primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-igase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 5

Identification of LP Genes of Interest

*Arabidopsis* wild type and the wri1 *Arabidopsis* mutant were used to identify LMP-encoding genes. The wri1 mutant is characterized by an 80% reduction in seed storage lipids (Focks & Benning, 1998, Plant Physiol. 118:91-101). The WRI1 gene has been cloned and described (Benning & Cernac, 2002, WO 02/072775 A2).

Other LMP candidate genes were identified by various *Arabidopsis thaliana* developmental or phytohormone mutants (e.g. obtained from EMS treatment or tDNA knock-out mutants) from the *Arabidopsis* stock center. These mutants and control wild-type plants were grown under standard conditions in growth chambers and screened for the accumulation of seed storage compounds. Mutants showing altered levels of seed storage compounds were considered as having a mutation in an LMP candidate gene and were investigated further. The sequences disclosed herein can comprise sequences encoding proteins and/or nucleic acids that affect the lipid composition and/or level in a plant. These can be independent of wri1 or they can also be targets of wri1 in that they are affected by expression of wri1. That effect can be either a decreased oil level or an increased oil level, or an alteration in the oil composition of a plant or part of a plant.

Example 6

Cloning of Full-ength cDNAs of Identified LMP Genes

Full-length cDNAs were isolated by RACE PCR using the SMART RACE cDNA amplification kit from Clontech allowing both 5'- and 3' rapid amplification of cDNA ends (RACE). The RACE PCR primers were designed based on the proprietary clone sequences. The isolation of full-length cDNAs and the RACE PCR protocol used were based on the manufacturer's conditions. The RACE product fragments were extracted from agarose gels with a QIAquick Gel Extraction Kit (Qiagen) and ligated into the TOPO pCR 2.1 vector (Invitrogen) following manufacturer's instructions. Recombinant vectors were transformed into TOP10 cells (Invitrogen) using standard conditions (Sambrook et al. 1989). Transformed cells were grown overnight at 37° C. on LB agar containing 50 µg/ml kanamycin and spread with 40 µl of a 40 mg/ml stock solution of X-gal in dimethylformamide for blue-white selection. Single white colonies were selected and used to inoculate 3 ml of liquid LB containing 50 µg/ml kanamycin and grown overnight at 37° C. Plasmid DNA is extracted using the QIAprep Spin Miniprep Kit (Qiagen) following manufacturer's instructions. Subsequent analyses of clones and restriction mapping was performed according to standard molecular biology techniques (Sambrook et al. 1989).

Full-length cDNAs were isolated and cloned into binary vectors by using the following procedure: Gene specific primers were designed using the full-length sequences obtained from *Arabidopsis* cDNA libraries or subsequent RACE amplification products. Full-length sequences and genes were amplified utilizing cDNA libraries as DNA template using touch-down PCR. In some cases, primers were designed to add an "AACA" Kozak-like sequence just upstream of the gene start codon and two bases downstream were, in some cases, changed to GC to facilitate increased gene expression levels (Chandrashekhar et al. 1997, Plant Molecular Biology 35:993-1001). PCR reaction cycles were: 94° C., 5 minutes; 9 cycles of 94° C., 1 minute, 65° C., 1 minute, 72° C., 4 minutes and in which the anneal temperature was lowered by 1° C. each cycle; 20 cycles of 94° C., 1 minute, 55° C., 1 minute, 72° C., 4 minutes; and the PCR cycle was ended with 72° C., 10 minutes. Amplified PCR products were gel purified from 1% agarose gels using GenElute-EtBr spin columns (Sigma) and after standard enzymatic digestion, were ligated into the plant binary vector pBPS-GB1 for transformation of *Arabidopsis*. The binary vector was amplified by overnight growth in *E. coli* DH5 in LB media and appropriate antibiotic and plasmid was prepared for downstream steps using Qiagen MiniPrep DNA preparation kit. The insert was verified throughout the various cloning steps by determining its size through restriction digest and inserts were sequenced to ensure the expected gene was used in *Arabidopsis* transformation.

Gene sequences can be used to identify homologous or heterologous genes (orthologs, the same LMP gene from another plant) from cDNA or genomic libraries. This can be done by designing PCR primers to conserved sequences identified by multiple sequence alignments. Orthologs are often identified by designing degenerate primers to full-length or partial sequences of genes of interest.

Gene sequences can be used to identify homologues or orthologs from cDNA or genomic libraries. Homologous genes (e.g. full-length cDNA clones) can be isolated via nucleic acid hybridization using for example cDNA libraries: Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. Aqueous solution hybridization and washing is performed at an ionic strength of 1 M NaCl and a temperature of 68° C. Hybridization probes are generated by e.g. radioactive (32P) nick transcription labeling (High Prime, Roche, Mannheim, Germany). Signals are detected by autoradiography.

Partially homologous or heterologous genes that are related but not identical can be identified in a procedure analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain of, for example, 10-20 amino acids, can be carried out by using synthetic radiolabeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by for example nick transcription. Hybridization is normally performed at low stringency conditions using high oligonucleotide concentrations.

Oligonucleotide hybridization solution:

6×SSC 0.01 M sodium phosphate 1 mM EDTA (pH 8)

0.5% SDS

100 µg/ml denatured salmon sperm DNA 0.1% nonfat dried milk

During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook et al. (1989, "Molecular Cloning: A Laboratory Manual," Cold Spring Harbor Laboratory Press) or Ausubel et al. (1994, "Current Protocols in Molecular Biology", John Wiley & Sons).

TABLE 3

A table of putative functions of the LMPs (Full length cDNA sequences can be found in the Appendix using the LMP name.)

| LMP | Function | ORF position |
|---|---|---|
| pk309 | acyl-(acyl carrier protein) thioesterase | 214-1299 |
| pk310 | Mitochondrial import inner membrane translocase subunit | 26-604 |
| pk311 | unknown protein | 31-1218 |
| pk312 | glycosyl transferase, putative | 38-1714 |
| pk313 | RNA binding like protein | 161-1464 |
| pk314 | Cdc-45 like protein | 294-2081 |
| pk315 | F-box family protein-related | 1-975 |
| pk316 | putative pyruvate kinase, plastid isozyme | 44-1756 |
| pk317 | pyruvate kinase | 135-1922 |
| pk318 | Hexokinase | 1-1488 |
| pk319 | pyruvate kinase | 138-1874 |

Example 7

Identification of Genes of Interest by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins can be used to produce specific antibodies for example by using standard techniques for rabbit immunization. Antibodies are affinity purified using a Ni-NTA column saturated with the recombinant antigen as described by Gu et al. (1994, BioTechniques 17:257-262). The antibody can then be used to screen expression cDNA libraries to identify homologous or heterologous genes via an immunological screening (Sambrook et al. 1989, Molecular Cloning: A Laboratory Manual," Cold Spring Harbor Laboratory Press or Ausubel et al., 1994, "Current Protocols in Molecular Biology," John Wiley & Sons).

Example 8

Northern-Hybridization

For RNA hybridization, 20 µg of total RNA or 1 µg of poly-(A)+ RNA is separated by gel electrophoresis in 1.25% agarose gels using formaldehyde as described in Amasino (1986, Anal. Biochem. 152:304), transferred by capillary attraction using 10×SSC to positively charged nylon membranes (Hybond N+, Amersham, Braunschweig), inunobilized by UV light and pre-hybridized for 3 hours at 68° C. using hybridization buffer (10% dextran sulfate w/v, 1 M NaCl, 1% SDS, 100 µg/ml of herring sperm DNA). The labeling of the DNA probe with the Highprime DNA labeling kit (Roche, Mannheim, Germany) is carried out during the pre-hybridization using alpha-32P dCTP (Amersham, Braunschweig, Germany). Hybridization is carried out after addition of the labeled DNA probe in the same buffer at 68° C. overnight. The washing steps are carried out twice for 15 minutes using 2×SSC and twice for 30 minutes using 1×SSC, 1% SDS at 68° C. The exposure of the sealed filters is carried out at −70° C. for a period of 1 day to 14 days.

Example 9

DNA Sequencing and Computational Functional Analysis cDNA libraries can be used for DNA sequencing according to standard methods, in particular by the chain termination method using the ABI PRISM Big Dye Terminator Cycle Sequencing Ready Reaction Kit (Perkin-Elmer, Weiterstadt, Germany). Random sequencing can be carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA can be prepared from overnight grown *E. coli* cultures grown in Luria-Broth medium containing ampicillin (See Sambrook et al. (1989, Cold Spring Harbor Laboratory Press: ISBN 0-87969-309-6) on a Qiagene DNA preparation robot (Qiagen, Hilden) according to the manufacturer's protocols). Sequences can be processed and annotated using the software package EST-MAX commercially provided by Bio-Max (Munich, Germany). The program incorporates bioinformatics methods important for functional and structural characterization of protein sequences. For reference, see http://pedant.mips.biochem.mpg.de.

The most important algorithms incorporated in EST-MAX are: FASTA: Very sensitive protein sequence database searches with estimates of statistical significance (Pearson, 1990, Rapid and sensitive sequence comparison with FASTP and FASTA. Methods Enzymol. 183:63-98); BLAST: Very sensitive protein sequence database searches with estimates of statistical significance (Altscbul et al., Basic local alignment search tool. J. Mol. Biol. 215:403-410); PREDATOR: High-accuracy secondary structure prediction from single and multiple sequences (Frishman & Argos, 1997, 75% accuracy in protein secondary structure prediction. Proteins 27:329-335); CLUSTALW: Multiple sequence alignment (Thompson et al., 1994, CLUSTAL W: improving the sensitivity of progressive multiple sequence alignment through sequence weighting, positions-specific gap penalties and weight matrix choice, Nucleic Acids Res. 22:4673-4680); TMAP: Transmembrane region prediction from multiply aligned sequences (Persson & Argos, 1994, Prediction of transmembrane segments in proteins utilizing multiple sequence alignments, J. Mol. Biol. 237:182-192); ALOM2: Transmembrane region prediction from single sequences (Klein et al., 1984, Prediction of protein function from sequence properties: A discriminant analysis of a database. Biochim. Biophys. Acta 787:221-226. Version 2 by Dr. K. Nakai); PROSEARCH: Detection of PROSITE protein sequence patterns. Kolakowski et al., 1992, ProSearch: fast searching of protein sequences with regular expression patterns related to protein structure and function. Biotechniques 13:919-921); BLIMPS: Similarity searches against a database of ungapped blocks (Wallace & Henikoff, 1992, PAT-MAT: A searching and extraction program for sequence, pattern and block queries and databases, CABIOS 8:249-254. Written by Bill Alford).

Example 10

Plasmids for Plant Transformation

For plant transformation binary vectors such as pBinAR can be used (Höfgen & Willmitzer 1990, Plant Sci. 66:221-230). Construction of the binary vectors can be performed by ligation of the cDNA in sense or antisense orientation into the T-DNA. 5' to the cDNA a plant promoter activates transcription of the cDNA. A polyadenylation sequence is located 3' to the cDNA Tissue-specific expression can be achieved by using a tissue specific promoter. For example, seed-specific expression can be achieved by cloning the napin or LeB4 or USP promoter 5' to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria, or endoplasmic reticulum (Kermode, 1996, Crit. Rev. Plant Sci. 15:285423). The signal peptide is cloned 5' in frame to the cDNA to achieve subcellular localization of the fusion protein.

Further examples for plant binary vectors are the pBPSGB1, pSUN2-GW, or pBPS-GB047 vectors into which the LMP gene candidates are cloned. These binary vectors contain an antibiotic resistance gene driven under the control of the AtAct2-I promoter and a seed-specific promoter or a constitutive promoter in front of the candidate gene with the NOSpA terminator or the OCS terminator. Partial or full-length LMP cDNAs are cloned into the multiple cloning site of the plant binary vector in sense or antisense orientation behind the USP or other seed-specific, tissue-specific, or constitutive promoters. The recombinant vector containing the gene of interest is transformed into Top10 cells (Invitrogen) using standard conditions. Transformed cells are selected for on LB agar containing 50 µg/ml kanamycin grown overnight at 37° C. Plasmid DNA is extracted using the QIAprep Spin Miniprep Kit (Qiagen) following manufacturer's instructions. Analysis of subsequent clones and restriction mapping is performed according to standard molecular biology techniques (Sambrook et al. 1989, Molecular Cloning, A Laboratory Manual. $2^{nd}$ Edition. Cold Spring Harbor Laboratory Press. Cold Spring Harbor, N.Y.).

Example 11

*Agrobacterium* Mediated Plant Transformation

*Agrobacterium* mediated plant transformation with the LMP nucleic acids described herein can be performed using standard transformation and regeneration techniques (Gelvin & Schilperoort, Plant Molecular Biology Manual, 2nd ed. Kluwer Academic Publ., Dordrecht 1995 in Sect., Ringbuc Zentrale Signatur:BT11-P; Glick, Bernard R and Thompson, John E. Methods in Plant Molecular Biology and Biotechnology, S. 360, CRC Press, Boca Raton 1993). For example, *Agrobacterium* mediated transformation can be performed using the GV3 (pMP90) (Koncz & Schell, 1986, Mol. Gen. Genet. 204:383-396) or LBA4404 (Clontech) *Agrobacterium tumefaciens* strain.

*Arabidopsis thaliana* can be grown and transformed according to standard conditions (Bechtold 1993, Acad. Sci. Paris. 316:1194-1199; Bent et al. 1994, Science 265:1856-1860). Additionally, rapeseed can be transformed with the LMP nucleic acids of the present invention via cotyledon or hypocotyl transformation (Moloney et al. 1989, Plant Cell Report 8:238-242; De Block et al. 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. Additionally, *Agrobacterium* mediated gene transfer to flax can be performed using, for example, a technique described by Mlynarova et al. (1994, Plant Cell Report 13:282-285).

Transformation of soybean can be performed using for example a technique described in EP 0424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) CLOROX supplemented with 0.05% (v/v) TWEEN for 20 minutes with continuous shaking. Then the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

The method of plant transformation is also applicable to *Brassica* and other crops. In particular, seeds of canola are surface sterilized with 70% ethanol for 4 minutes at room temperature with continuous shaking, followed by 20% (v/v) CLOROX supplemented with 0.05% (v/v) TWEEN for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige & Skoog 1962, Physiol. Plant. 15:473-497) medium supplemented with 100 mM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The inhibition of dry embryos with a culture of *Agrobacterium* is also applicable to maize embryo axes).

The embryos are removed from the inhibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol $m^{-2}s^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol $m^{-2}s^{-1}$ light intensity and 12 h photoperiod for about 80 days.

Samples of the primary transgenic plants ($T_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR as recommended by the manufacturer.

Example 12

In Vivo Mutagenesis

In vivo mutagenesis of microorganisms can be performed by incorporation and passage of the plasmid (or other vector) DNA through *E. coli* or other microorganisms (e.g. *Bacillus* spp. or yeasts such as *Saccharomyces cerevisiae*), that are impaired in their capabilities to maintain the integrity of their genetic information Typical mutator strains have mutations in the genes for the DNA repair system (e.g., mutHLS, mutd, mutT, etc.; for reference, see Rupp, 1996, DNA repair mechanisms, in: *Escherichia coli* and *Salmonella*, p. 2277-2294, ASM: Washington.) Such strains are well known to those skilled in the art The use of such strains is illustrated, for example, in Greener and Callahan 1994, Strategies 7:32-34. Transfer of mutated DNA molecules into plants is preferably done after selection and testing in microorganisms. Transgenic plants are generated according to various examples within this document.

Example 13

Assessment of the mRNA Expression and Activity of a Recombinant Gene Product in the Transformed Organism The activity of a recombinant gene product in the transformed host organism can be measured on the transcriptional and/or on the translational level. A useful method to ascertain the level of transcription of the gene (an indicator of the amount of mRNA available for translation to the gene product) is to perform a Northern blot (for reference see, for example, Ausubel et al., 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues, or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label, which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar et al., 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In Vitro Analysis of the Function of *Arabidopsis thaliana* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon & Webb, 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3rd ed. Academic Press: New York; Bisswanger, H., (1994) Enzymkinetik, 2nd ed. VCH: Weinheim (ISBN 3527300325); Bergmeyer, H. U., Bergmeyer, J., Graβl, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH: Weinheim, p. 352-363.

Example 15

Analysis of the Impact of Recombinant Proteins on the Production of a Desired Seed Storage Compound The effect of the genetic modification in plants on a desired seed storage compound (such as a sugar, lipid, or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon et al., 1987, Applications of HPLC in Biochemistry in: Laboratory Techniques in Biochemistry and Molecular Biology, vol. 17; Rehm et al., 1993, Product recovery and purification, Biotechnology, vol. 3, Chapter III, pp. 469-714, VCH: Weinheim; Belter, P. A. et al., 1988 Bioseparations: downstream processing for biotechnology, John Wiley & Sons; Kennedy & Cabral, 1992, Recovery processes for biological materials, John Wiley and Sons; Shaeiwitz & Henry, 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX,307 S.—(Oily Press Lipid Library; and "Progress in Lipid Research, Oxford:Pergamon Press, 1 (1952)—16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as described by Christie and references therein (1997 in: Advances on Lipid Methodology 4th ed.: Christie, Oily Press, Dundee, pp. 119-169; 1998). Detailed methods are described for leaves by Lernieux et al. (1990, Theor. Appl. Genet. 80:234-240) and for seeds by Focks & Benning (1998, Plant Physiol. 118:91-101).

Positional analysis of the fatty acid composition at the sn-1, sn-2 or sn-3 positions of the glycerol backbone is determined by lipase digestion (See, e.g., Siebertz & Heinz 1977, Z. Naturforsch. 32c:193-205, and Christie 1987, Lipid Analysis $2^{nd}$ Edition, Pergamon Press, Exeter, ISBN 0-08-023791-6).

Total seed oil levels can be measured by any appropriate method. Quantitation of seed oil contents is often performed with conventional methods, such as near infrared analysis (NIR) or nuclear magnetic resonance imaging (NMR). NIR spectroscopy has become a standard method for screening seed samples whenever the samples of interest have been amenable to this technique. Samples studied include canola, soybean, maize, wheat, rice, and others. NIR analysis of single seeds can be used (See, e.g., Velasco et al., 'Estimation of seed weight, oil content and fatty acid composition in intact single seeds of rapeseed (*Brassica napus* L.) by near-infrared reflectance spectroscopy, 'Euphytica, Vol. 106, 1999, pp. 79-85). NMR has also been used to analyze oil content in seeds (See, e.g., Robertson & Morrison, "Analysis of oil content of sunflower seed by wide-line NMR, "Journal of the American Oil Chemists Society, 1979, Vol. 56, 1979, pp. 961-964, which is herein incorporated by reference in its entirety).

A typical way to gather information regarding the influence of increased or decreased protein activities on lipid and sugar biosynthetic pathways is for example via analyzing the carbon fluxes by labeling studies with leaves or seeds using $^{14}C$-acetate or $^{14}C$-pyruvate (See, e.g., Focks & Benning, 1998, Plant Physiol. 118:91-101; Eccleston & Ohlrogge, 1998, Plant Cell 10:613-621). The distribution of $^{14}C$ into lipids and aqueous soluble components can be determined by liquid scintillation counting after the respective separation (for example on TLC plates) including standards like $^{14}C$-sucrose and $^{14}C$-malate (Eccleston & Ohlrogge, 1998, Plant Cell 10:613-621).

Material to be analyzed can be disintegrated via sonication, glass milling, liquid nitrogen and grinding or via other applicable methods. The material has to be centrifuged after disintegration. The sediment is resuspended in distilled water, heated for 10 minutes at 100° C., cooled on ice, and centrifuged again, followed by extraction in 0.5 M sulfuric acid in methanol containing 2% dimethoxypropane for 1 hour at 90° C. leading to hydrolyzed oil and lipid compounds, resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes, and then 5 minutes at 240° C. The identity of resulting fatty acid methylesters is defined by the use of standards available form commercial sources (i.e., Sigma). In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt et al. (1989, Methods Enzymol. 174:518-552; for other methods, see also Härtel et al., 1998, Plant Physiol. Biochem. 36:407-417 and Focks & Benning, 1998, Plant Physiol. 118:91-101).

For the extraction of soluble sugars and starch, 50 seeds are homogenized in 500 µl of 80% (v/v) ethanol in a 1.5-ml polypropylene test tube and incubated at 70° C. for 90 minutes. Following centrifugation at 16,000 g for 5 minutes, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µl of 0.2 N KOH, and the suspension is incubated at 95° C. for 1 hour to dissolve the starch. Following the addition of 35 µl of 1 N acetic acid and centrifugation for 5 minutes at 16,000 g, the supernatant is used for starch quantification.

To quantify soluble sugars, 10 µl of the sugar extract is added to 990 µl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoisomerase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found by Bradford (1976, Anal. Biochem. 72:248-254). For quantification of total seed protein, 15-20 seeds are homogenized in 250 µl of acetone in a 1.5-ml polypropylene test tube. Following centrifugation at 16,000 g, the supernatant is discarded, and the vacuum-dried pellet is resuspended in 250 µL of extraction buffer containing 50 mM Tris-HCl, pH 8.0, 250 mM NaCl, 1 mM EDTA, and 1% (w/v) SDS. Following incubation for 2 hours at 25° C., the homogenate is centrifuged at 16,000 g for 5 minutes, and 200 ml of the supernatant will be used for protein measurements. In the assay, globulin is used for calibration. For protein measurements, Lowry DC protein assay (Bio-Rad) or Bradford-assay (Bio-Rad) is used.

Enzymatic assays of hexokinase and fructokinase are performed spectrophotometrically according to Renz et al. (1993, Planta 190:156-165), of phosphogluco-isomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase, and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Hartel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al., 2000, Nature Biotech 18:1447-1161). For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid, or fatty acid contents.

Similarly, plant expression vectors comprising the nucleic acids disclosed herein, or fragments thereof can be constructed and transformed into an appropriate plant cell such as *Arabidopsis*, soybean, rapeseed, rice, maize, wheat, *Medicago truncatula*, etc., using standard protocols. The resulting transgenic cells and/or plants derived from the cells can then be assayed for alterations in sugar, oil, lipid, or fatty acid contents.

Additionally, the sequences disclosed herein, or fragments thereof, can be used to generate knockout mutations in the genomes of various organisms, such as bacteria, mammalian cells, yeast cells, and plant cells (Girke at al., 1998, Plant J. 15:39-48). The resultant knockout cells can then be evaluated for their composition and content in seed storage compounds, and the effect on the phenotype and/or genotype of the mutation. Other methods of gene inactivation include those described in U.S. Pat. No. 6,004,804 and Puttaraju et al. (1999, Nature Biotech. 17:246-252).

Example 16

Purification of the Desired Product from Transformed Organisms

An LMP can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin, while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey & Ollis, 1986, Biochemical Engineering Fundamentals, McGraw-Hill:New York).

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60:133-140), Malakhova et al. (1996, Biotekhnologiya 11:27-32), and Schmidt et al. (1998, Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587), and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Example 17

Screening for Increased Stress Tolerance and Plant Growth

The transgenic plants are screened for their improved stress tolerance demon-strating that transgene expression confers stress tolerance. The transgenic plants are further screened for their growth rate demonstrating that transgene expression confers increased growth rates and/or increased seed yield.

Increased seed size might be reflected in an increased seed weight of gene overexpressors. Increased seed size leads to greater yield in many economically important crop plants. Therefore, increased seed size is one goal of genetically engineering and selection using LMPs as described in this application.

For in vitro root analysis square plates measuring 12 cm×12 cm can be used. For each plate, 52 ml of MS media (0.5×MS salts, 0.5% sucrose, 0.5 g/L MES buffer, 1% Phytagar) without selection will be used. Plates will be allowed to dry in the sterile hood for one hour to reduce future condensation. Seed aliquots will be sterilized in glass vials with ethanol for 5 minutes, ethanol will be removed, and the seeds are allowed to dry in the sterile hood for one hour.

Seeds will be spotted in the plates using the Vacuseed Device (Lehle). After the seeds are spotted on the plates, the plates will be wrapped with Ventwrap and placed vertically in racks in the dark at 4° C. for four days to stratify the seeds. The plates are transferred to a C5 Percival Growth Chamber and placed vertically. The growth chamber conditions will be 23° C. day/21° C. night and 16 hour day/8 hour night. For data collection, a high-resolution flatbed scanner is used. Analysis of the roots is done using the WinRhizo software package.

A comparison of the root length obtained with *Arabidopsis* wild type and the wri1 mutant indicated a significant reduction in root length in wri1 mutants. This reduction in root length was found to be associated with a delayed germination and a reduced number of leaves at a defined time point of development as compared with the wild type. Overexpression of genes involved in the WRI1 regulatory network in wild type background may improve seed germination, increase root length, and increase speed of leaf development and number of leaves. The latter may improve photosynthetic performance of plants resulting in increase yield of biomass and in increased amounts and/or size of seeds associated with increased amounts of seed storage compounds like oil, protein, and sugars.

For soil root analysis, seeds may be imbibed at 4° C. for 2 days in water and planted directly in soil with no selection. Deepots (Hummert D40) will be used with a saturated peat pellet (Jiffy 727) at the base and filled with water saturated Metromix. After planting, pots will be covered with plastic wrap to prevent drying. Plants may be grown using only water present at media preparation, as the water in the soil in these large pots is sufficient for 3 weeks of growth, and encourages rapid root growth. The plastic wrapping of the pots will be removed after 12 days and morphological data documented. At day 17, the aerial parts of the plant will be harvested, dried (65° C. for 2 days), and dry weight measured. To examine the roots the peat pellet will be pushed towards the top of the pot to remove the soil and roots as a unit. The soil will then be separated from the roots in a tray and the maximum root length will be measured. Root length of all plants for all transgenic lines will be averaged and compared against the average of the wild type plants.

Those skilled in the art will recognize, or will be able to ascertain using no more than routine experimentation, many equivalents to the specific embodiments of the invention described herein. Such equivalents are intended to be encompasses by the claims to the invention disclosed and claimed herein.

APPENDIX

Nucleic acid sequence of pk309 (SEQ ID NO: 1)
```
TGACAATTGTCCATCATCAATGGCATTAAATGGCAAAACCGTAATTTCGA
ACTCCACCAAGGGGCAAACTTAAAAGTCGATGTCTTTCTTCTTCACCTCG
GACCCATCGGAGAGAAGATACTACTAGAAGAGATTCATTCACAGTGTTGA
AATTAAAAAACCGAAACTTTCTCGTTTCTTCTTCTTCTTCTCCAATTTTC
AAAATTCGAAAAGATGTTGAAGCTTTCGTGTAATGTGACTGATTCTAAGT
TACAGAGAAGCTTACTCTTCTTCTCCCATTCATATCGATCTGATCCGGTG
AATTTCATCCGTCGGAGAATTGCTCTTGTTCTCAGACGAAGAAGACAGGT
TTGGTTCCTTTGCGTGCTGTTGTATCTGCTGATCAAGGAAGTGTGGTTCA
AGGTTTGGCTACTCTCGCGGATCAGCTCCGATTAGGTAGTTTGACTGAAG
ATGGTTTATCTTATAAAGAGAAGTTTGTTGTTAGATCTTACGAAGTGGGT
AGTAACAAAACCGCTACTGTTGAAACCATTGCTAATCTTTTACAGGAGGT
GGGATGTAATCATGCACAAAGTGTTGGTTTTTCGACTGATGGGTTTGCAA
CAACAACTACTATGAGGAAGTTGCATCTCATTTGGGTTACTGCGAGAATG
CATATCGAGATCTATAAGTACCCTGCTTGGGGTGATGTGGTTGAGATAGA
GACTTGGTGTCAGAGTGAAGGAAGGATTGGGACAAGGCGTGATTGGATTC
TTAAGGATTCTGTCACTGGTGAAGTCACTGGCCGTGCTACAAGCAAGTGG
GTGATGATGACCAAGACACGAGACGGCTTCAGAAAGTTTCTGATGATGTT
CGGGACGAGTACTTGGTCTTCTGTCCTCAAGAACCGAGGTTAGCATTTCC
GGAAGAGAATAACAGAAGCTTGAAGAAAATCCCGAAACTCGAAGATCCGG
CTCAGTATTCAATGATTGGGCTTAAGCCTAGACGAGCTGATCTCGACATG
AACCAGCATGTCAATAATGTCACCTATATTGGATGGGTTCTCGAGAGCAT
ACCACAAGAAATTGTAGACACGCACGAGCTTCAGGTCATAACTCTGGATT
ATAGAAGAGAATGTCAACAAGACGATGTGGTGGATTCACTCACCACCACC
ACCTCTGAAATTGGTGGAACCAATGGCTCTGCCACGTCTGGCACACAGGG
CCACAACGATAGCCAGTTCTTGCACCTCCTGAGGTTGTCTGGAGATGGTC
AGGAGATCACCGCGGGACAACTCTGTGGAGAAAGAAGCCTTCAATTTAAG
AAATAGACAATGTCTTTAGCCATTTTGTTCTCAAGTTTCCATCATCTCAA
TGAAGATTTCGCTTCACGAGTCTGAGCAGGTCTCCATTTTTTTCTCTTTC
AAGTTTGGGTTAGACTAGAGGGAACTGGATTGTTGGAGTATTAATCTTTG
TTGAATTTCATTATGTTTGTTCATGTTTTTGTACAAATTTTGGGGATTTA
GCCAAACCCATATCGTCTTTGGTCTTGTCTTGTGCCTGCGTGTATTTTTA
ATCTATCCGTTCAAAACACAGATTGTTCATTAGATGTTTTATATAAACAG
AGTTAAAGACCTGA
```

Nucleic acid sequence of pk310 (SEQ ID NO: 2)
```
GAAATTGGAGTTCTCTCGAAGTTCCGTGGCGTCAAAAATGGCGTTGGGTG
ATCGGAAATCCCCAGAACAAACAAATCAGGCGTTATCTCCTCCGACGCCT
ATTGTGCAQGGAAATGGAACTCCGACGAAGCGTGTGTTGATCACTTCCCT
TTTAGCAGGAGTAATTGGTGGAGGAGCTGGTTTAGTGTCTAAACACCGGA
TAGCTCATCCCAATATTCCTACTGTTTACGCTGCTAATTTTGCTATTGTC
GCCGGTTGCTATTGCGGAGCTCGTGAATCTGTGAGAATAACTCGAAGATC
AGAACACGATGATTTAATGAACTCAGCTATTGGAGGACTTTTTAGTGGTG
CTTTGCTTGGAAGACTTCAAGGAGGTCCTAAGGGTGCGATTCGCTACTCT
CTAGTTTTTGCTGCTGTAGGCACAGCATTTGATTATGCTACCCTTAAAGG
AAAACCAATGTTAGAGAGCTACCGTAACATGGAGTCATTCAAGTTACCTG
AATGGTCTCCTATTAAAGTCCTCGACGAAGAAGCCTTAGCAAAGAAGAAA
GCTCATGAAGAGAAGATATTCCCTGAAAGAGTCCTCGGCAAATTGAACAA
AGAATAGTCTTAACCAACTTAAGATTATTTCTCTTTTGCCCCCATAAATT
TCTTAAGTTGGAATTTTGTTTATCGGTGATGTTTCGTGAAAGACTGAAAG
TAATTCCAGACCTTGTAGATGAGACTTGAGGAGGATTTTGGTTTTTTGTT
GTTTCCTCAAGGTAAAAATTTTCTTGAGACATAAGAAAACATCTTTGTAT
GCTGACCTACCCATAAAGCGTATATATTCATGGTTAATTATGGGCTTA
```

Nucleic acid sequence of pk311 (SEQ ID NO: 3)
```
GTTTTTCTCCACAAGTTTTTTCTGCAAACATGTCTGAACTTGCATTGTCA
TCTCAAGAAGAGTCTCCAAGTAGTAATAAGATTGGTTTATCTTCTCTTCT
TCTCTCTGACTTTCATCTCTTTTGCTCATTTATCCTCACTCACCCTTTCT
ATTTTTCTTACTTGCTCTTCTTTTCACCTTACATCTTCAAGATTCTCTCT
TTTCTTTCACCACTCTTTGTCACCACCACACTCTTGCTTCTTGCCTTATT
```

APPENDIX-continued

```
GAGTACTTTACATGTTCAAGCACTTGTCTCGACTCTGAATCACTAGAAA
CACAACCAAGCTTCCTTTTCTCCTTTTGTAGTAAGCTTGGAAGTGTCTTG
GAACACAAGTTTGATGTCAACAATGAGGGTTTTAAGTCATTGGAGGAGTT
GGAAGCGTATAAGATGGTCGTCGAGGCTTGCTCGATGGAATGTGCGTCCG
AGAATGAGATATGTTCGGATGAATTGACGTTTGTTGACAAATTCTGTAGC
CATGAGAGCACGGTGTCGGAATCTTTGACCGATGAGACCCTTGAGGAGCA
AGTTGAGATCCAACCGTTGAAGTTTGAGGATGTGATTGTTTTGGAGAAAG
AAGAAGAAACCAAGAAATGTGAAAAGGAAGAAGTAGAAGAACAAAAAGTC
AAGCATAAAAGTGACGTTGTCCTCGATAACAGAGAAGAGCCGACAAAAGA
AGAATCCAAAGCTCAAAAGTTGACCTTGTCGGAGATAGTAATAATGAAA
GTTATGATCTCCCAAAACTGAGCAATTTTCTCGGAGAAGGAGAAGGTAAA
AGAAATGTAGTGACTAAGAACGAAGAAGAAGATAATGTTTCTCTCCAAAG
CTTTGGATCAATGAGAAAAGAGAAAGAATGGAGGAGAACATTGGCTTGCA
AGCTATTTGAAGAACGACACAATGCTGACGTTGGACAAGGCATGGATCAG
CTGTGGGAGACTTACGAGACACAAACAGAGAAGAAGCAGCAAACCGAAGA
AGAGAAGAAGAAGCTCAAGAAGAAGACGAAGTCGATGATGAAGACAAAGA
GTATAGAGAAGGAAGTTATAGTGGAGGAGGAAGATGATGATGGGATTGAT
CATCAGCAACTTTGTTGTTTACAAGCTTTGAAGTTCTCAACAGGGAAGAT
GCATTTGGGAATTGCGAGGCCTAACCTTTTGAAGCTATCTAAGGCTTTCA
AAGGCATTGGACGTTTTTACAATGCTAACAAACATTCCAAGAAAGCTTGA
AAAGGAGATGAATAATAAAACTTTGTATTAATTGGGATCTATAAACAATG
TAACTTGTAAGTTTCCATTGTTTTGGGCAAGTTCTATGAACAATGTAAGG
GAAAATAAAGGTAAAGGCTAGGATTTTGCCATATGTGTTTAGCTTTGAT
CTTAACTTTCTTTCCTATCCTTGTATATTTTGGGACGGATAACCCGTAAT
GGCCCGTATCGATTGAG
```

Nucleic acid sequence of pk312 (SEQ ID NO: 4)
```
ACACTGTGAGATTCAAGTGTAAAGTGCTCTCTCCCCAATGGCTAATCACC
ACCGACTTTTACGCGGCGGCGGATCTCCGGCCATAATCGGTGGCAGAATC
ACACTCACAGCTTTCGCTTCCACTATCGCACTCTTCCTCTTCACTCTCTC
CTTCTTCTTCGCTTCAGATTCTAACGATTCTCCTGATCTCCTTCTTCCCG
GTGTTGAGTACTCTAATGGAGTCGGATCTAGAAGATCCATGTTGGATATC
AAATCGGATCCGCTTAAGCCACGGTTGATTCAGATCCGGAAACAAGCTGA
TGATCATCGGTCATTAGCATTAGCTTTATGCTTCTTACGCGAGAAAGCTTA
AGCTCGAGAATTCGAAACTCGTCAGGATCTTCGCTGATCTTTCGAGGAAT
TACACGGATCTGATTAACAAACCGACGTATCGAGCTTTGTATGATTCTGA
TGGAGCCTCGATTGAAGAATCTGTGCTTAGGCAATTTGAGAAAGAAGTTA
AGGAACGGATTAAAATGACTCGTCAAGTGATTTGCTGAAGCTAAAGAGTCT
TTTGATAATCAGTTGAAGATTCAGAAGCTGAAAGATACGATTTTCGCTGT
TAACGAACAGTTAACTAATGCTAAGAAGCAAGGTGCGTTTTCGAGTTTGA
TCGCTGCGAAATCGATTCCGAAAGGATTGCATTGTCTTGCTATGAGGCTG
ATGGAAGAGAGGATTGCTCACCCTGAGAAGTATACTGATGAAGGGAAAGA
TAGACCGCGGGAGCTCGAGGATCCGAATCTTTACCATTACGCTATATTTT
CGGATAATGTGATTGCGGCTTCGGTGGTTGTGAACTCTGCTGTGAAGAAT
GCTAAGGAGCCGTGGAAGCATGTTTTTCACGTTGTGACTGATAAGATGAA
TCTGGAGCTATGCAGGTTATGTTTAAACTCTATGATGAGGGAGCTCA
TGTAGAAGTTAAAGCTGTTGAGGATTATACGTTTTTGAACTCTTCGTATG
TGCCTGTGTTGAAGCAGTTAGAATCTGCGAATCTTCAGAAGTTTTATTTC
GAGAATAAGCTCGAGAATGCGACGAAAGATACCACGAATATGAAGTTCAG
GAACCCCAAGTATTTATCTATATTGAATCACTTGAGGTTTTATTTACCCG
AGATGTACCCGAAACTACATAGGATACTGTTTTTGACGATGATGTGGTT
GTGCAGAAGGATTTAACGGGTCTGTGGGAGATTGATATGGATGGGAAAGT
GAATGGAGCTGTAGAGACTTGTTTTGGGTCGTTTCATCGGTACGCTCAAT
ACATGAATTTCTCACATCCTTTGATCAAAGAGAAGTTTAATCCCAAAGCA
TGTGCGTGGGCGTATGGAATGAACTTCTTTGATCTTGATGCTTGGAAGAG
AGAAGAGTGCACAGAAGAATATCACTACTGGCAAAATCTGAACGAGAACA
GGGCTCTATGGAAACTGGGGACGTTACCACCGGGACTGATCACCTTTTAC
TCAACCACAAAGCCGCTGGACAAATCATGGCATGTGCTTGGGCTGGGTTA
CAATCCGAGCATTAGCATGGATGAGATCCGCAACGCTGCAGTGGTACACT
TCAACGGTAACATGAAGCCATGGCTTGACATAGCTATGAACCAGTTCGA
CCACTTTGGACCAAACACGTCGACTATGACCTCGAGTTTGTTCAGGCTTG
CAATTTTGGCCTCTGAACTATGAAAATTTTCTTTATCATCAAAAATCTGA
AAGCATATGTTGTTTGTTACTTCACGCTCTACGAAGTTTTAACCTTAGTTT
TTGTTTGTGTTTATTTATATATTTTTGGGGGTTTAGTAGAACACTTGTAT
TTTGTTCATAGCTATCTTTGTTCTATGCAACCTATAATCAAAGCTTATT
ATAAAGTCACATTATGCC
```

Nucleic acid sequence of pk313 (SEQ ID NO: 5)
```
TTTTTTTCTTCTTCTTCCATTTTTTGTTCTCACGTCGCTCTCTCTTTTT
TTCGAGATTCAGCTGTAAAACCCTAACTAGCGCCATAGCCAAGGAAGCTT
TCCTCAGATCGTCTCTCCGAAATTTTCCGGTTAATCGTCAGTTAAGGGGA
AAATTAGGCTATGGCGATGTTAGGTGCACAGCAAGTTCCAGCAGCAGCTT
GTACTCCAGATATGGTTGGGAATGCTTTTGTGCCCCAGTATTATCACATA
TTGCATCAATCACCTGAGCATGTTCACAGATTTTACCAAGAGATTAGCAA
GTTAGGTCGTCCTGAAGAGAATGGTTTAATGAGCATCACTTCTACCTTCG
AAGCTATTGACAAGAAGATAATGGCGCTTGGTTACGGTGTAATCAGTGCA
GAGATAGCTACTGTGGACACACAAGATCTCATGGAGGTGGTTATATTGT
ACTGGTGACTGGGTATTTGACGGGAAAAGACAGTGTCAGGAGGACGTTTA
GTCAGACCTTCTTCCTTGCTCCACAGGAGACAGGATACTTTGTCTTGAAT
GATATGTTTCGATTCATTGATGAAGGCACTGTCGTACATGGAAATCAGAT
```

Nucleic acid sequence of pk314 (SEQ ID NO: 6)
```
GAAAAGAAATCAAATACCTTCAGATCTCTATCTTCCTCATTCACACACCCT
CTCTCTCTTCTCTCCTTTTCTCTTCTCCTTTTCTCTATCTCCCTCTTTGT
CCGTTCGCATCCTCTAATCATCGTCAACAAGCCGACGAAGAGAGAAACGA
ATCCAAAGTTCGTTACTTGAAAGCTACCCAGAAGAATTCAAATCTCAGGT
ACTTTTCCTGTGGATTTGATCTGGGCACTGCTTATTAGGGATTTGATTGG
ATCTACAAAATTCTGCCTTCTGGGTGATTCAATTTCACGGAAATGGTGAG
GATTAGAAAGTAGAATCGTTCTACGCGAAGCTTCGTGAGTCAGCTACTT
CATTATCTTCACGAATCCACTTTTGATATTCCTTCAACATCTGATGTT
GATTCACTTTGTGCGCTTAAGGTTATTACTCATATCCTTGAATCAGATTC
GATTCAGTATTCTTGTTTCCCTGTATCGTCTTTTTTGGAGATTCACAAGT
ATGCTGGTCCTGCTGGTTTGTGTTCTACTTCGTTGGAGAGTCCTCCTGTT
ACTATACTGTTGATTAATTGGGGTTGTCACCGTGATTTGAAGCTTGTGTT
GAAGTTAGGTCCTTCGGCTCGTGTTTTCGTTGTTGATAGTGATAGGGCTA
TTCATTTGCATAATCTTAGTGATTATAATGAGCAAGTTGTTGTTCTTCAT
ACTGATGATGATGAGGACGAAGGTGATTTGGCTTATGATTTCGATGTGTT
GAAATTGGCGAATGAGAGCTTTCAGTTACGTGTAGAAGATGCTGGTGAAG
AATCTGATGAGGAGGAGGAAGATGAGGAAGGATGAGGAGGATGATGAT
GATGATGATGGTGATAGGCCAAGTAAGAGGAGGAAAATGGGAGATGGTGT
GAAGGTTTTCAAGAAGCTAAAGAGATTATTACAAGATGGGACTTTTCA
TGGGAAGCCATCGGGGTGTTTGTTGTTTGAGCTATCTCATATGTTGAGGA
AGAACACTAACGAGTTGTTGTGGCTGGCTTGTGTTTCTTTGACTGATCAG
TTTGTTCATGAGAGGTTGACTGATGAAAGATATCAAGCTGCGGTTATGGA
GCTTGAACAACATCAATAAGCTCAGGGAATATAGATAAGATCACTAGTG
TTACTCTGAAAGATGGAACCAAGGTTCGAGCACCAGACTGTTCAAGAATC
TCTTATGAAGAAGAGCCTAGGCTTATGCTTCTTAGAGAGTGGACGTTGTT
TGACTCCATGCTTTGTTCTTCATACATTGCGACTAAGTTGAAGACATGGA
GTGATAACGGTATCAAGAAACTTAAGCTTCTTCTTCTAGCGCGTATGGGATTT
GCACTTATCGAGTGTCAGCAAAAGTTTCCGTACATGAGCCTTGAGGTGAA
GAGGAAGATGAAGCAAGAGTTTGATCGGTTTTTGCAGAATATGGGCTTAA
TGATTTCTACTACCGGAGTTTCTTGCGGCTTCATGTTATAGCTCAAGGGT
CTCTGCTGCAGATGTTGTCTATGGTATTACAGCACTTCTTGAATCATTTT
TGGGTCAGGTGGCTCCTCTGCTTCAAAACAGTTTGGTGAAGCTTATGATG
CTCTGTCTTTGAACAATTTGGATAAACTTCGATCTGGGATGCAACAAGCA
ATCAAGGTTCAACGAGCAATTCTTAGACAAGGAAGTGCAGCAATCACTAA
AAGTGGATGCATTCGAAGTGGTAGGAAATTCAGATGGTAAAGATTGAAGA
TTCAATGGATGCGAAGTATTTGGGATATCCTCAGGCCTTAACAAAATTCT
GTTACTTTCTGATGGATGCTTTGAGAGAGAAAGGAGCTAGGATGAAACCA
ATGCATGTGCCTGCGCATCTCAACAACCTGGGAAGATACTCGTGGTTGG
GGTTTGTGGGAAACCGAGGCTCGGGGCAGTCAGAGGGAATGCTTTTGGCA
ATGCTTTTCAGGAGCAGCTCAAGAAGTAGAAGTAGAGCTGATTACTTTCACGAG
CTATTCGAGTCTTCTTGGATTGTCTTGGATGCTTCTGCAGTTAACTCTTT
CATGATTAGATTAACCGAGAAGCTCTGACATAGTCTCATTGTTCTTCGAT
TCAGTGTGTTTTCTTTTATAGTTTTCAGTTTTATCTCACTGTTTGCATTT
TTTACGAGCCTGTGTAATAGGCACAATCTGTTATCAATCATGTAACTTGT
TTAAT
```

Nucleic acid sequence of pk315 (SEQ ID NO: 7)
```
ATGCAAATAGGTCAAGCCTTAGCCGCAGCAAAGGAAGGTGAGTCTCAGAT
GATCGTGATGATGGGTAACAATCTTTCTTTAACAAGCATTATTCTCAATG
GAGATCCATCTATAGAGCATAAAGGAAAACTTACTTGCCTTGACGAACAA
GTCAAGATATCCAGTTCTATCACTGCGAGGGCTTACTGCTATGCATTTT
AAAAGATGATTCTAGGTTTGTGGTTTGTAATCCGTATTTGGAGCAAACAA
GGTGGATCGAACCAAGATATTCCCATCGTCCATACGGAATGGATAGGTTC
```

TCTTACGCTCTTGGATACGTGAATACGGATTCTTGTCGTAGCTACAAGTT
GTTGAGGTTTATAGATTATTACTACAATGCACCCGAGAAGCAATTCTTTT
GGTATGAAGTCTACGATTTTGACTCTGATTTATGGACTACTCTTGATGTC
ACTCCACATTGGCGTATAGCGTTTTGTAACACTGGCGTTCCTTTTAAGGG
AAACACTTACTGGTGTGCTGCAGAAAGGAACGTAGATGTAGATGAAGTCT
TAGCTAACGCTTAATCTGTTTTGATTTTACAAAAGAGAAGCTTGCGTTTT
TACTTCAGCACGATGAATCAAATCCATATGAGCTTGACTTGTGGATTACA
ACTAAGATTGAGACAGAAGAGGTGTTGTGGAGCAAGTTCTTGAGAGTGGA
AACAGCTGGTTTTAATAGTTATGTTCCTTTTATAAGTGGAAGTTTCTTCA
TTGACGAGGAGAAGAAAGTCGCCTTTGGTTTTGATGAACGTAACCGCCAG
AGAGTTATTGTCATTGGAGAGGCTGGATACTTGAGGGGATTGGATCTCGT
TGGGGATTTTGGAGACCAAAGCTGTAAGCCAGATCTATGCTCTTATGTTC
CAAGTTTAGTGCAAATCAAGCAACCTGAAGGAGGGGAAAGGGAAGAAGAA
AGCGAATATGGAGAAGCTTCGATATGA

Nucleic acid sequence of pk316 (SEQ ID NO: 8)
GTCTCTCCTCTGCATCTCCTCTGTTCCTCAGGTTTCTCTGCTCATGGCTG
CTTATGGTCAAATCTCCTCGGGAATGACTGTAGATCCTCAGGTTCTCTCT
TCCTCCAGAAACATTGGAGTTTCCCTATCACCTCTCCGGAGAACACTAAT
CGGCGCCGGAGTTAGGTCTACTAGTATCTCTCTCCGTCAATGTTCTCTCT
CCGTTAGATCGATTAAATCTCCGAAGATAGCCGCAAACTAAAGCTTATG
CAGAGAACGGTGCTTTTGATGTGGGAGTTTTGGATTCTTCATCATATAGA
TTGGCTGATTCAAGAACAAGTAGTAATGATTCAAGGAGGAAGACTAAGAT
TGTGTGTACGATTGGACCGTCTTCGAGTTCTAGGGAAATGATTTGGAAAC
TCGCGGAAGCTGGAATGAATGTGCTCGTTTGAATATGTCTCATGGTGAT
CATGCTTCTCATCAGATAACTATTGATTTAGTTAAGGAGTATAATTCTTT
GTTTGTTGACAAAGCTATTGCTATTATGTTGGATACAAAGGGTCCTGAGG
TTCGAAGCGGGGATGTACCGCAGCCGATATTTCTTGAAGAGGGTCAAGAG
TTTAACTTTACTATCAAGAGAGGTGTTTCGCTTAAAGACACTGTTAGTGT
AAATTATGATGATTTTGTGAACGATGTTGAAGTTGGGGATATACTTTTGG
TGGATGGTGGAATGATGTCGTTAGCTGTTAAATCAAAGACGAGTGATTTG
GTGAAGTGTGTGGTTATTGATGGTGGAGAGCTTCAATCTAGACGTCACTT
GAATGTTCGAGGAAAGAGTGCGACTCTTCCATCCATTACAGACAAAGATT
GGGAAGACATAAAATTTGGAGTGGACAACCAAGTCGATTTCTACGCGTCT
CCTTTGTTAAGGATGCTAAAGTTGTCCATGAGTTGAAGAACTATCTCAAA
ACCTGCAGTGCAGACATATCGGTGATTGTGAAAATTGAAAGTGCAGACTC
TATAAAGAATCTTCCTTCTATCATATCTGCTTGTGATGGGGCAATGGTTG
CTCGTGGAGATCTTGGAGCTGAACTTCCCATTGAAGAGGTCCCGTTGTTA
CAGGAAGAAATAATCAGAAGGTGTAGAGACATTCATAAACCAGTGATTGT
TGCCACAAACATGCTAGAGAGTATGATTAATCATCCAACGCCTACAAGAG
CTGAAGTCTCTGACATTGCAATTGCAGTACGTGAAGGCGCAGATGCTATC
ATGCTTTCTGGTGAAACCGCACATGGAAAGTTTCCGCTGAAAGCTGTTAA
CGTAATGCATACTGTGCGTTGAGAACCGAGGCAAGTCTACCTGTCAGAA
CCTCGGCATCCCGTACCACTGCTTACAAGGGTCACATGGGCCAAATGTTT
GCTTTTCATGCTTCTATAATGGCAAATACACTGAGCTCACCGCTAATTGT
ATTTACGAGAACCGGATCCATGGCAGTGCTTCTAAGCCACTACCGCCAT
CTGCAACAATTTTCGCCTTCACAAACCAGAGAAGAATAATGCAAAGGCTT
GCTCTTTATCAAGGTGTCATGCCTATATATATGGAGTTCTCGGATGATGC
AGAAGATACATATGCCCGGTCTCTCAAACTCTTACAGGACGAGAATATGC
TCAAGGAAGGACAACATGTAACTCTTGTCCAAAGTGGCTCGCAACCCATT
TGGCGTGAAGATCAACACATCTCATCAAGTCCGTAAGATAAAGATAGG
TGGATGATGTTTTACTTCTTGAGCTACACAAACATCTTGCTTTTACTCAG
CTTTCTTTCTCTTACACAGTTCGATCCATATTTTTTGAATCACTCACAG
TGAATCAAACAACCCATATAAATTTTAAGTTATTGAAGCTTTTTTTCTGTT
ATAG Nucleic acid sequence of pk317 (SEQ ID NO: 9)
AGAAAAAAAAAAAAAAATCCAAATTCAAGACTCTCACACTTCGATATCTC
CGCCTTCATTCTCCTCAGAGCCAACTGTCCTGAGATTTCGATTTCGATTT
CTCCGATCTCTCTTCCTCCGTCGCCGGCGAAACCATGTCTCAGTCTATTC
AATTCTCCACTCCTTCACACACTCCTCACCTTCTCCATCTCCCTCACTCA
CAATTCAACCGTCCTCTCTCCTCTATCTCCTTCCGTCGCTTCCCTCTAAC
AACCATCAAATACACTTCCATCAGAGCCTCCTCGTCATCATCTCCTTCAC
CGGATCTCGATTCATCGTCCTCATCATCATCCTCGCAAGTACTTCTCTCA
CCTAACGGTACTGGTGCTGTGAAGCTGATGAGAGATCCGTTGTCGCTAC
GGCGGTTACGACTGATACGTCTGGGATTGAGGTTGATACTGTGACGAAG
CTGAGCTTAAGGAGAATGGATTTAGAAGTACGAGGGAGCAGAAGATTGCT
TGTACGATCGGACCGGCTGACTTGTGGATTTGAGCAGCTTGAGGCGCTTGC
TGTGGGAGGTATGAATGTGGCAAGGCTTAATATGTGTCACGGTACGCGTG
ATTGGCACCGCGGTGTGATTCGTAGTGTTCGGAGGCTTAATGAGGAGAAA
GGCTTTGCGGTGCTATTATGATGGATACTGAAGGTAGTGAGATTCATATG
GGAGATCTTGGTGGTGAAGCTTCAGCTAAAGCAGAGGATGGTGAGGTTTG
GACTTTCACTGTTAGACTTTGATTCTTCGTCCTGAACGTACCATTA
GTGTTAGCTACGATGGTTTCGCTGAAGATGTAAGAGTTGGGGATGAACTT
TTGGTTGATGGTGGAGATTGGAGTTTGAAGTGATTGAAGAAGATTGGTCC
TGATGTTAAGTGTCTATGTACCGATCCTGGATTGTTGCTTCCTCGAGCTA
ACTTGACGTTTTGGAGAGATGGAAGTCTTGTACGAGAGCGTAATGCCATG
CTTCCAACAATTTCTTCCAAGGACTGGTTGGATATTGATTTTGGAATTGC
TGAAGGTGTGGATTTCATTGCTGTATCGTTTGTCAAGTCGGCTGAAGTCA
TTAATCACCTTAAAAGTTATCTTGCTGCTCGTTCCCGTGGAGGGGAAATT GGAGTGATTGCAAAGATCGAGAGTATCGATTCACTGACCAATTTGGAAGA
AATTATTCTAGCATCAGATGGGCCATGGTTGCAAGAGGAGATCTGGGAG
CTCAGATACCTCTTGAGCAAGTTCCAGCAGCTCAACAGAGAATCGTCCAA
GTATGCAGAGCTCTTAACAAACCCGTCATGTCGCTTCACAGCTATTGGAG
TCCATGATTGAGTACCCAACTCCAACCAGAGCAGAAGTTGCCGACGTGTC
TGAAGCAGTAAGACAAAGATCAGATGCATTGATGCTCTCTGGAGAATCAG
CTATGGGACAATTCCCAGACAAGGCGCTCACGGTTCTAAGGACTGTCAGT
TTAAGAATCGAGAGATGGTGGAGGGAAGAGAAACGCCATGAGTCTGTACC
GCTTCAAGCCATAGGCTCTTCATTTTCAGACAAAATCTCAGAAGAGATCT
GTAACTCAGCTGCTAAAATGGCTAACAATCTTGGAGTGGACGCGGTTTTC
GTTTACACAACGAGCGGACACATGGCATCACTGGTCTCCCGATGTCGCCC
GGACTGCCCGATCTTTGCTTTCACAACCACAACCTCAGTGAGAGACGCT
TAAACCTACAATGGGGACTTATCCCATTCCGTCTCAGCTTCTCAGACGAC
ATGAAAGCAACTTGAACAAAACATTCTCGTTACTGAAATCAAGAGGTAT
GATCAAATCTGGTGACCTCGTGATCGCAGTCTCGGACATGCTGCAATCAA
TCCAGGTAATGAACGTCCCGTAATTCTCTCTCTTTTATACAATTCGCAA
TCCCGCAAAGAGTGTTTGTTTCCTACTTTTGTTACTGTTTTAGACTA
CTCTTACATTAGATTCCAGAGGCATCATCATCTCCGGTTTGTTAACAACA
GTAATGTGTAAGCTTTGTTTGTAGTGTGTACTGTTTGTTTTTGGTTTTCA
ATAAATATCAGTAATCTTATTCAAATATTCGATTCTATC Nucleic acid sequence of pk318 (SEQ ID NO: 10)
ATGGGTAAAGTAGCTGTTGGAGCGACTGTTGTTTGCACGGCGGCGGTTTG
TGCGGTGGCTGTTTTGGTTGTTCGACGACGGATGCAGAGCTCAGGGAAGT
GGGGACGTGTTTGGCTATCCTCAAGGCCTTTGAAGAGGATTGTGCGACT
CCGATCTCGAAACTGAGACAAGTGGCTGATGCTATGACCGTTGAGATGCA
TGCTGGTCTTGCATCCGACGTGGTAGCAAACTCAAGATGCTTATCAGCT
ACGTTGATAATCTTCCTTCCGGGGATGAAAAGGGTCTCTTTATGCATTG
GACCTAGGGGGGACAAACTTCCGTGCTCATGCGTGTGCTTCTTGGCCGGAA
GCAAGAGCGTGTTGTTAAACAAGAATTCGAAGAAGTTTCGATTCCTCCTC
ATTTGATGACTGGTGGTTCAGATGAGTTGTTCAATTTTATAGCTGAAGCT
CTTGCGAAGTTTGTCGCTACAGAATGCGAAGACTTTCATCTTCCAGAAGG
TAGACAGAGGGAATTGGTTTCACTTTCTCGTTTCCTGTTAAGCAGATT
CTCTGTCCTCTGGTAGTCTCATCAAATGGACAAAAGGCTTTTCCATCGAA
GAAGCAGTTGGACAAGATGTTGTTGGAGCACTTAATAAGGCTCTGGAAAG
AGTTGGTCTTGACATGCGAATCGCAGCACTTGTTAATGATACCGTTGGAA
CACTACCGGTGGTAGATACTATAACCCGGATGTTGTTGCTGCTGTTATT
TTAGGCACTGGGACAAACGCAGCCTATGTTGAGCGTGCAACCGCGATCCC
TAAATGGCATGGTCTGCTTCCAAAATCAGGAGAAATGGTTATAACATGG
AATGGGAACTTCAGGTCATCACATCTTCCATTAACCGAGTTTGATCAC
ACGCTGGATTTCGAGAGTCTGAATCCAGGCGAACAGATTCTTGAGAAAAT
CATTTCCGGTATGTACTTGGGAGATTTTGCGAAGAGTTCTTCTAAAGA
TGGCTGAAGATGCTGCTTCTTTGGCATACAGTCCCATCTAAGCTGAGA
ATACCATTCATCATTAGGACTCCTCACATGTCGGCTATGCACAACGACAC
TTCTCCAGACTTGAAGATTGTTGGGAGCAAGATTAAGGATATATTGGAGG
TCCCTACAACTTCTCTGAAAATGAGAAAGTTGTGATCAGTCTCTGCAAC
ATCATAGCAACCCGGAGCTCGTCTCTCTGCTGCTGGAATCTATGGTAT
TCTGAAGAAACTGGGAAGAGATACTACTAAAGACGAGGAGGTGCAGAAAT
CGGTTATAGCCATGGATGTGGATTGTTTGAGCATTACACTCAGTTTAGT
GAGTGTATGGAGAGCTCACTAAAAGATTGCTTGGAGATGAAGCTTCAGG
AAGCGTTGAAGTCACTCACTCCAATGATGGATCAGGCATTGGAGCTGCGC
TTCTTGCTGCTTCTCACTCTCTACCTTGAAGACTCTTAA Nucleic acid sequence of pk319 (SEQ ID NO: 11)
AAGCACTTCTTCTCCGCCTTCGTAAGTTCCGCCGAAAAGAACCAAATCCT
CACTACTCTGTCTCAGCTTTCGACCTCTCTCTTCTCATTCCTTTGCAACT
TCTCACTTCTCGAATTCCTTCTCTTCAAAATCAGAAATGGCTCAAGTGGT
TGCTACCAGGTCAATTCAAGGCTCGATGTTATCTCCCAACGGTGGATCTG
TGTCTACAAGATCCGAGAAGCTATTGAAACAGCGAGTTTTGCAGTGAAG
GTTCTTGGCAACGAAGCAAAGAGAAGTGGAAGAGTCTCTGTAAGAAGCAG
AAGAGTGGTTGATACTACTGTGAGATCCGCTCGTGTTGAGACTGAAGTCA
TTCCTGTTTCTCCTGAAGATGTGCCTAACAGAGAGGAGCAGCTTGAGAGG
TTGTTGGAAATGCAACAAGTTTGGTGATACATCGGTAGGGATGGTGTCGAA
GCCGACAGTGAGGAGGAAGACAAAGATTGTTTGCACCGTTGGTCCGTCGA
CCAACACACAGAAATGATATGGAATTGGCTGAAGCTGGGATGAATGTT
GCTAGGATGAATATGTCTCATGGAGATCATGCTTCACATAAGAAGGTTAT
TGATTTGGTTAACAATGCACAAACTAAAGACACTCATTATTGCTA
TCATGCTTGACACCAAGGGTCCGGAAGTTAGGAGTGGAGATTTACCTCAG
CCAATTATGTTAGATCCTGGTCAAGAGTTTACCTTTACAATTGAGAGAGG
AGTCAGCACACCAAGTTGTGTCAGTGTTAACTATGATGATTTCGTTAATG
ACGTGGACGGGTGACATCTTCTTGTTGATGGTGATGATCGTTT
ATGGTGAAGTCAAAGACAAAGACTCTGTCAAATGTGAAGTTGTTGATGG
TGGAGAACTTAAGTCAAGGAGACACCTGAATGTCCGAGGAAAGAGTGCAA
CTTTACCTTCAATCACTGAGAAGGACTGGGAGGATATTAAATTTGGAGTG
GAGAACAAAGTTGCTTTTATGCAGTTTCCTTTGTCAAGATGCTCAAGT
TGTACACGAGTTGAAGAAATACCTTTCAAAATGATGGTGCTGATATACAC
GTGATAGTGAAAATTGAGTGCAGACTCCATACCTAACTTGCACTCCAT
TATCACAGCATCAGATGGCAATGGTTGCAAGAGGTGATCTTGGTGCAG
AGCTTCCAATTGAAGAAGTCCCCATTCTTCAGGAGGAGATCATTAACCTG
TGCCGTAGTATGGGAAAAGCTGTTATTGTTGCGACTAACATGCTTGAGAG APPENDIX-continued

```
TATGATAGTTCATCCAACTCCAACCCGGGCAGAGGTCTCAGACATTGCTA
TCGCTGTTAGAGAAGGTGCTGATGCGGTAATGCTTTCAGGAGAAACTGCT
CACGGAAAGTTCCCATTGAAAGCTGCTGGAGTGATGCACACTGTTGCATT
GCGAACAGAAGCAACCATTACTAGCGGTGAAATGCCACCTAATCTTGGTC
AAGCCTTCAAGAACCATATGAGTGAGATGTTTGCATACCATGCAACCATG
ATGTCAAACACACTTGGAACTTCAACTGTTGTCTTCACCAGAACCGGTTT
CATGGCCATATTGTTAAGTCACTATCGTCCTTCCGGCACAATCTATGCCT
TCACAAATGAGAAAAAAATACAACAAAGATTAGCTTTGTATCAAGGTGTA
TGCCCCATATATATGGAGTTCACAGATGATGCAGAAGAAACTTTTGCTAA
```

APPENDIX-continued

```
TGCTTTGGCTACATTACTGAAACAAGGAATGGTGAAGAAGGGAGAGGAAA
TAGCAATCGTACAGAGCGGTACACAGCCAATCTGGCGATCTCAATCGACA
CATAACATCCAAGTCCGCAAGGTTTAAAGCTTCTTTTAAGATGGGATGTC
TTTAATATGTAGAACCTCGTTTTTGGTTATAATTTTCGTTGCATGTCTCT
CTTCTCTTGTACTATTCACACTTGTTGTTTGCTGTATCTTCTTCTTCAGT
TTGCTTTGCTACGATTGTGGTTTTTGGAGACATTATAGCTCATTAACTGT
TTGTGAGACCAAATGTGTCAGAATCCGCTATT
```

We claim:

1. A method of increasing fatty acid content in a seed of a plant relative to a corresponding control plant comprising,
   i) transforming a plant or plant cell with an expression vector comprising a lipid metabolism protein (LMP) nucleic acid;
   ii) generating from the plant cell a transgenic plant; and
   iii) selecting a plant having increased fatty acid content in a seed relative to a corresponding control plant;
   wherein the nucleic acid comprises a polynucleotide sequence selected from the group consisting of:
   a) the polynucleotide sequence of SEQ ID NO:11;
   b) a polynucleotide sequence encoding a polypeptide comprising an amino acid sequence that is encoded by the polynucleotide sequence of SEQ ID NO:11;
   c) a polynucleotide sequence having at least 95% sequence identity with the full-length LMP nucleic acid of a) or b) above; and
   d) a polynucleotide sequence that hybridizes under stringent conditions to the full-length LMP nucleic acid of a) or b) above, wherein the stringent conditions comprise one or more washes in 0.2×SSC, 0.1% SDS at 50-65° C.

2. The method of claim 1, wherein the LMP nucleic acid comprises the polynucleotide sequence of SEQ ID NO:11.

3. The method of claim 1, wherein the LMP nucleic acid comprises a polynucleotide sequence encoding a polypeptide comprising an amino acid sequence that is encoded by the polynucleotide sequence of SEQ ID NO:11.

4. The method of claim 1, wherein the LMP nucleic acid comprises a polynucleotide sequence having at least 95% sequence identity with the polynucleotide sequence of a) or b) of claim 1.

5. The method of claim 1, wherein the LMP nucleic acid hybridizes under stringent conditions to the LMP nucleic acid of a) or b) of claim 1, wherein the stringent conditions comprise one or more washes in 0.2×SSC, 0.1% SDS at 50-65° C.

6. The method of claim 1, wherein the level of total oil content in a seed is increased.

7. The method of claim 1, wherein the level of a seed storage compound is increased in the transgenic plant as compared to an untransformed wild type variety of the plant.

8. The method of claim 1, wherein the LMP nucleic acid is operatively linked to a heterologous promoter selected from the group consisting of a seed-specific promoter, a root-specific promoter, and a non-tissue-specific promoter.

9. A method of for increasing fatty acid content in a seed of a plant relative to a corresponding control plant comprising, increasing the expression of a Lipid Metabolism Protein (LMP) nucleic acid in the plant, and selecting a plant having increased fatty acid content in a seed relative to a corresponding control plant, wherein the LMP nucleic acid comprises a polynucleotide sequence selected from the group consisting of:
   a) the polynucleotide sequence of SEQ ID NO:11;
   b) a polynucleotide sequence encoding a polypeptide comprising an amino acid sequence that is encoded by the polynucleotide sequence of SEQ ID NO:11;
   c) a polynucleotide sequence having at least 95% sequence identity with the full-length LMP nucleic acid of a) or b) above; and
   d) a polynucleotide sequence that hybridizes under stringent conditions to the full-length LMP nucleic acid of a) or b) above, wherein the stringent conditions comprise one or more washes in 0.2×SSC, 0.1% SDS at 50-65° C.

10. The method of claim 9, wherein the level of total oil content in a seed is increased.

11. A transgenic plant made by the method of claim 1 and having increased fatty acid content in a seed relative to a corresponding control plant, wherein the transgenic plant comprises the nucleic acid.

12. The transgenic plant of claim 11, wherein the plant is a dicotyledonous plant.

13. The transgenic plant of claim 11, wherein the plant is a monocotyledonous plant.

14. The transgenic plant of claim 11, wherein the plant is a high oil producing plant.

15. The transgenic plant of claim 14, wherein the high oil producing plant is selected from the group consisting of rapeseed, canola, linseed, soybean, sunflower, maize, oat, rye, barley, wheat, pepper, tagetes, cotton, oil palm, coconut palm, flax, castor, and peanut.

16. The method of claim 9, wherein the LMP nucleic acid comprises a polynucleotide sequence having at least 95% sequence identity with the polynucleotide sequence of a) or b) of claim 9.

17. The method of claim 1, further comprising obtaining a plant, part of the plant or progeny thereof comprising the nucleic acid and having increased fatty acid content relative to a corresponding control plant or part thereof.

18. The method of claim 3, further comprising obtaining a plant, part of the plant or progeny thereof comprising the nucleic acid and having increased fatty acid content relative to a corresponding control plant or part thereof.

19. The method of claim 9, further comprising obtaining a plant, part of the plant or progeny thereof comprising the nucleic acid and having increased fatty acid content relative to a corresponding control plant or part thereof.

20. The method of claim 16, further comprising obtaining a plant, part of the plant or progeny thereof comprising the nucleic acid and having increased fatty acid content relative to a corresponding control plant or part thereof.

21. A transgenic plant made by the method of claim 3 and having increased fatty acid content in a seed relative to a corresponding control plant, wherein the transgenic plant comprises the nucleic acid.

* * * * *

SEQUENCE LISTING

<160> NUMBER OF SEQ ID NOS: 11

<210> SEQ ID NO 1
<211> LENGTH: 1617
<212> TYPE: DNA
<213> ORGANISM: Arabidopsis thaliana

<400> SEQUENCE: 1

```
tgacaattgt ccatcatcaa tggcattaaa tggcaaaacc gtaatttcga actccaccaa      60
ggggcaaact aaaagtcga tgtctttctt cttcacctcg gacccatcgg agagaagata     120
ctactagaag agattcattc acagtgttga aattaaaaaa ccgaaacttt ctcgtttctt     180
cttcttcttc tccaatttc aaaattcgaa agatgttga agctttcgtg taatgtgact      240
gattctaagt tacagagaag cttactcttc ttctcccatt catatcgatc tgatccggtg     300
aatttcatcc gtcggagaat tgtctcttgt tctcagacga agaagacagg tttggttcct     360
ttgcgtgctg ttgtatctgc tgatcaagga agtgtggttc aaggtttggc tactctcgcg     420
gatcagctcc gattaggtag tttgactgaa gatggtttat cttataaaga gaagtttgtt     480
gttagatctt acgaagtggg tagtaacaaa accgctactg ttgaaaccat tgctaatctt     540
ttacaggagg tgggatgtaa tcatgcacaa agtgttggtt tttcgactga tgggtttgca     600
acaacaacta ctatgaggaa gttgcatctc atttgggtta ctgcgagaat gcatatcgag     660
atctataagt accctgcttg gggtgatgtg gttgagatag agacttggtg tcagagtgaa     720
ggaaggattg ggacaaggcg tgattggatt cttaaggatt ctgtcactgg tgaagtcact     780
ggccgtgcta caagcaagtg ggtgatgatg aaccaagaca cgagacggct tcagaaagtt     840
tctgatgatg ttcgggacga gtacttggtc ttctgtcctc aagaaccgag gttagcattt     900
ccggaagaga ataacagaag cttgaagaaa atcccgaaac tcgaagatcc ggctcagtat     960
tcaatgattg ggcttaagcc tagacgagct gatctcgaca tgaaccagca tgtcaataat    1020
gtcacctata ttggatgggt tctcgagagc ataccacaag aaattgtaga cacgcacgag    1080
cttcaggtca taactctgga ttatagaaga gaatgtcaac aagacgatgt ggtggattca    1140
ctcaccacca ccacctctga aattggtgga accaatggct ctgccacgtc tggcacacag    1200
ggccacaacg atagccagtt cttgcacctc ctgaggttgt ctggagatgg tcaggagatc    1260
aaccgcggga caactctgtg gagaaagaag ccttcaagtt aagaaataga caatgtcttt    1320
agccatttg ttctcaagtt tccatcatct caatgaagat ttcgcttcac gagtctgagc    1380
aggtctccat ttttttctct ttcaagtttg ggttagacta gagggaactg gattgttgga    1440
gtattaatct tgttgaatt tcattatgtt tgttcatgtt tttgtacaaa ttttggggat    1500
ttagccaaac ccatatcgtc tttggtcttg tcttgtgcct gcgtgtattt ttaatctatc    1560
cgttcaaaac acagattgtt cattagatgt tttatataaa cagagttaaa gacctga      1617
```

```
<210> SEQ ID NO 2
<211> LENGTH: 848
<212> TYPE: DNA
<213> ORGANISM: Arabidopsis thaliana

<400> SEQUENCE: 2
gaaattggag ttctctcgaa gttccgtggc gtcaaaaatg gcgttgggtg atcggaaatc      60
cccagaacaa acaaatcagg cgttatctcc tccgacgcct attgtgcagg aaaatggaac     120
tccgacgaag cgtgtgttga tcacttccct tttagcagga gtaattggtg gaggagctgg     180
tttagtgtct aaacaccgga tagctcatcc caatattcct actgtttacg ctgctaattt     240
tgctattgtc gccggttgct attgcggagc tcgtgaatct gtgagaataa ctcgaagatc     300
agaacacgat gatttaatga actcagctat tggaggactt tttagtggtg ctttgcttgg     360
aagacttcaa ggaggtccta agggtgcgat tcgctactct ctagtttttg ctgctgtagg     420
cacagcattt gattatgcta cccttaaagg aaaaccaatg ttagagagct accgtaacat     480
ggagtcattc aagttacctg aatggtctcc tattaaagtc ctcgacgaag aagccttagc     540
aaagaagaaa gctcatgaag agaagatatt ccctgaaaga gtcctcggca aattgaacaa     600
agaatagtct taaccaactt aagattattt ctcttttgcc cccataaatt tcttaagttg     660
gaattttgtt tatcggtgat gtttcgtgaa agactgaaag taattccaga ccttgtagat     720
gagacttgag gaggattttg gttttttgtt gtttcctcaa ggtaaaaatt ttcttgagac     780
ataagaaaac atctttgtat gctgacctac ccataaagcg tatatattca tggttaatta     840
tgggctta                                                             848

<210> SEQ ID NO 3
<211> LENGTH: 1468
<212> TYPE: DNA
<213> ORGANISM: Arabidopsis thaliana

<400> SEQUENCE: 3 gttttttctcc acaaggtttt ttctgcaaac atgtctgaac ttgcattgtc atctcaagaa      60
gagtctccaa gtagtaataa gattggttta tcttctcttc ttctctctga cttcatctc     120
ttttgctcat ttatcctcac tcaccctttc tatttttctt acttgctctt cttttcacct     180
tacatcttca agattctctc ttttctttca ccactctttg tcaccaccac actcttgctt     240
cttgccttat tgagtacttt acatgttcaa gacacttgtc tcgactctga atcactagaa     300
acacaaccaa gcttccttt ctcctttgt agtaagcttg gaagtgtctt ggaacacaag     360
tttgatgtca acaatgaggg ttttaagtca ttggaggagt tggaagcgta agatggtc     420
gtcgaggctt gctcgatgga atgtgcgtcc gagaatgaga tatgttcgga tgaattgacg     480
tttgttgaca aattctgtag ccatgagagc acggtgtcgg aatctttgac cgatgagacc     540
cttgaggagc aagttgagat ccaaccgttg aagtttgagg atgtgattgt tttggagaaa     600
gaagaagaaa ccaagaaatg tgaaaaggaa gaagtagaag aacaaaaagt caagcataaa     660
agtgacgttg tcctcgataa cagagaagag ccgacaaaag aagaatccaa agctcaaaaa     720
gttgaccttg tcggagatag taataatgaa agttatgatc tcccaaaact gagcaatttt     780
ctcggagaag gagaaggtaa aagaaatgta gtgactaaga acgaagaaga agataatgtt     840
tctctccaaa gctttggatc aatgagaaaa gagaaagaat ggaggagaac attggcttgc     900
aagctatttg aagaacgaca caatgctgac gttggacaag gcatggatca gctgtgggag     960
acttacgaga cacaaacaga gaagaagcag caaaccgaag aagagaagaa gaagctcaag    1020
```

| | |
|---|---:|
| aagaagacga agtcgatgat gaagacaaag agtatagaga aggaagttat agtggaggag | 1080 |
| gaagatgatg atgggattga tcatcagcaa ctttgttgtt tacaagcttt gaagttctca | 1140 |
| acagggaaga tgcatttggg aattgcgagg cctaaccttt tgaagctatc taaggctttc | 1200 |
| aaaggcattg gacgttttta caatgctaac aaacattcca agaaagcttg aaaaggagat | 1260 |
| gaataataaa actttgtatt aattgggatc tataaacaat gtaacttgta agtttccatt | 1320 |
| gttttgggca agttctatga acaatgtaag ggaaaataaa aggtaaaggc taggattttg | 1380 |
| ccatatgtgt ttagctttga tcttaacttt ctttcctatc cttgtatatt ttgggacgga | 1440 |
| taacccgtaa tggcccgtat cgattgag | 1468 |

<210> SEQ ID NO 4
<211> LENGTH: 1919
<212> TYPE: DNA
<213> ORGANISM: Arabidopsis thaliana

<400> SEQUENCE: 4

| | |
|---|---:|
| acactgtgag attcaagtgt aaagtgctct ctccccaatg gctaatcacc accgactttt | 60 |
| acgcggcggc ggatctccgg ccataatcgg tggcagaatc acactcacag ctttcgcttc | 120 |
| cactatcgca ctcttcctct tcactctctc cttcttcttc gcttcagatt ctaacgattc | 180 |
| tcctgatctc cttcttcccg gtgttgagta ctctaatgga gtcggatcta aagatccat | 240 |
| gttggatatc aaatcggatc cgcttaagcc acggttgatt cagatccgga acaagctga | 300 |
| tgatcatcgg tcattagcat tagcttatgc ttcttacgcg agaaagctta agctcgagaa | 360 |
| ttcgaaactc gtcaggatct tcgctgatct ttcgaggaat tacacggatc tgattaacaa | 420 |
| accgacgtat cgagctttgt atgattctga tggagcctcg attgaagaat ctgtgcttag | 480 |
| gcaatttgag aaagaagtta aggaacggat taaaatgact cgtcaagtga ttgctgaagc | 540 |
| taaagagtct tttgataatc agttgaagat tcagaagctg aaagatacga ttttcgctgt | 600 |
| taacgaacag ttaactaatg ctaagaagca aggtgcgttt cgagtttga tcgctgcgaa | 660 |
| atcgattccg aaaggattgc attgtcttgc tatgaggctg atggaagaga ggattgctca | 720 |
| ccctgagaag tatactgatg aagggaaaga tagaccgcgg gagctcgagg atccgaatct | 780 |
| ttaccattac gctatatttt cggataatgt gattgcggct tcggtggttg tgaactctgc | 840 |
| tgtgaagaat gctaaggagc cgtggaagca tgtttttcac gttgtgactg ataagatgaa | 900 |
| tcttggagct atgcaggtta tgtttaaact gaaggagtat aaaggagctc atgtagaagt | 960 |
| taaagctgtt gaggattata cgtttttgaa ctcttcgtat gtgcctgtgt tgaagcagtt | 1020 |
| agaatctgcg aatcttcaga agttttattt cgagaataag ctcgagaatg cgacgaaaga | 1080 |
| taccacgaat atgaagttca ggaaccccaa gtatttatct atattgaatc acttgaggtt | 1140 |
| ttatttaccc gagatgtacc cgaaactaca taggatactg ttttggacg atgatgtggt | 1200 |
| tgtgcagaag gatttaacgg tctgtggga gattgatatg gatgggaag tgaatggagc | 1260 |
| tgtagagact tgttttgggt cgtttcatcg gtacgctcaa tacatgaatt tctcacatcc | 1320 |
| tttgatcaaa gagaagttta atcccaaagc atgtgcgtgg gcgtatggaa tgaacttctt | 1380 |
| tgatcttgat gcttggagaa gagagaagtg cacagaagaa tatcactact ggcaaaatct | 1440 |
| gaacgagaac agggctctat ggaaactggg gacgttacca ccgggactga tcaccttta | 1500 |
| ctcaaccaca aagccgctgg acaaatcatg gcatgtgctt gggctggtt acaatccgag | 1560 |
| cattagcatg gatgagatcc gcaacgctgc agtggtacac ttcaacggta acatgaagcc | 1620 |
| atggcttgac atagctatga accagtttcg accactttgg accaaacacg tcgactatga | 1680 |

```
cctcgagttt gttcaggctt gcaattttgg cctctgaact atgaaaattt tctttatcat    1740
caaaatctga aagcatatgt tgtttgttac ttcagctcta cgaagtttta accttagttt    1800
ttgtttgtgt ttatttatat attttgggg gtttagtaga acacttgtat tttgttcata     1860
gctatctttg ttctatggca acctataatc aaagcttaat tataaagtca cattatgcc     1919

<210> SEQ ID NO 5
<211> LENGTH: 1831
<212> TYPE: DNA
<213> ORGANISM: Arabidopsis thaliana

<400> SEQUENCE: 5
tttttttctt cttcttccat ttttttgttc tcacgtcgct ctctcttttt ttcgagattc      60
agctgtaaaa ccctaactag cgccatagcc aaggaagctt tcctcagatc gtctctccga    120
aattttccgg ttaatcgtca gttaagggga aaattaggct atggcgatgt taggtgcaca    180
gcaagttcca gcagcagctt gtactccaga tatggttggg aatgcttttg tgccccagta    240
ttatcacata ttgcatcaat cacctgagca tgttcacaga ttttaccaag agattagcaa    300
gttaggtcgt cctgaagaga atggtttaat gagcatcact tctaccttgc aagctattga    360
caagaagata atggcgcttg gttacggtgt aatcagtgca gagatagcta ctgtggacac    420
acaagaatct catggaggtg ttatattgt actggtgact gggtatttga cgggaaaaga     480
cagtgtcagg aggacgttta gtcagacctt cttccttgct ccacaggaga caggatactt    540
tgtcttgaat gatatgtttc gattcattga tgaaggcact gtcgtacatg gaaatcagat    600
tccagtgaac aacgtccaag ctcctgtcaa cacttaccag gacacagctg ctgcgaagga    660
aattccagat gactttgttc aggagaaata tgtccaagag aatcatgctg ttaagcaaac    720
cgaggtgttg tccaagagca ttaatgagcc tgaaaaagtg ttcacgccct ctgaagatga    780
acaagtatca gctgcagaag aagctctggt gactgaaaca gttaatgaag caccaattga    840
agtgcaaaag gttggagaat ctgattctag gactggcgaa attccaaaga gatcttatgc    900
atcaattgtg aaggttatga agaaaaatgc tgcaccaatg tctgcttcga gaactccaac    960
aaaggtggaa ccaaagaaac aagaagatca agccattcat atccctctac caacaccatt   1020
gtctgagaaa tcagattcag gagcaaatgt tgctgtaaat gagaacaatc aagagaatga   1080
aagagctcta ggtccatcca tctatctaaa gggtttaccc cttgatgcaa cacctgcctt   1140
gcttgagaat gagttccaga aatttggact tattaggacc aatggaattc aagtgagaag   1200
ccagaaggga ttctgttttg gttttgttga gtttgaatcc gcaagttcca tgcaaagcgc   1260
tatcgaggca tcacctgtca tgctcaatgg acacaaagtt gttgtggagg aaaagcgatc   1320
taccgcaaga gggaactata gaggacgttc gacgtttggt gtaaacacag gctacagaaa   1380
cgaaggagga aggggtcgtg ggagctttgg aggtggaaga ggaggatatg ccggaccga    1440 tttcaacgga tatggtaata acaggggaaa caatagaggc ggatacgcaa accgagcaaa   1500
tggtgatggt ggtgggttcc cgagggccaa tggtaacaat ggacgagtaa dacgtggtgg   1560
cggaaatgat gctaacagag ctacgaaacc cgtggatgat gctccccgtg tgtctgttgc   1620 tgccgtaaatg tgcttttgaa acaaaaagct ctattggttt tagagagttt aggcgtagag   1680
caatggcaaa aaaaaacact attattttct tttcactgtg tcgccatttt attaattgga   1740
gtcaaaactt gagagcaaga gagagtttcg tcggttcttg cttgtctatt ttttcttcac   1800
tgctaatgaa atctctttct tcatgtggct c                                   1831

<210> SEQ ID NO 6
```

```
<211> LENGTH: 2211
<212> TYPE: DNA
<213> ORGANISM: Arabidopsis thaliana

<400> SEQUENCE: 6
gaaagaaatc aaatacctcc agatctctat cttcctcatt cacacaccct ctctctcttc      60
tccttttctc tcttctcctt ttctctatct ccctctttgt tccgttcgca tcctctaatc     120
atcgtcaaca agccgacgaa gagagaaacg aatccaaagt tcgttacttg aaagctaccc     180
agaagaattc aaatctcagg tacttttcct gtggatttga tctgggcact gcttattagg     240
gatttgattg gatctacaaa attctgcctt ctgggtgatt caatttcacg gaaatggtga     300
ggattaagaa agtagaatcg ttctacgcga agcttcgtga gtcagctact tcattatctt     360
cacagaatcc acttttgata tttccttcaa catctgatgt tgattcactt tgtgcgctta     420
aggttattac tcatatcctt gaatcagatt cgattcagta ttcttgtttc cctgtatcgt     480
cttttttgga gattcacaag tatgctggtc ctgctggttt tgttctact tcgttggaga     540
gtcctcctgt tactatactg ttgattaatt ggggttgtca ccgtgatttg aagcttgtgt     600
tgaagttagg tccttcggct cgtgttttcg ttgttgatag tcataggcct attcatttgc     660
ataatcttag tgattataat gagcaagttg ttgttcttca tactgatgat gatgagaggc     720
aaggtgattt ggcttatgat ttcgatgtgt tgaaattggc gaatgagagc tttcagttac     780
gtgtagaaga tgctggtgaa gaatctgatg aggaggagga agatgaggaa gaggatgagg     840
aggatgatga tgatgatgat ggtgatagc caagtaagag gaggaaaatg ggagatggtg     900
tgaaggtttt caagaagcta agagggatt attacaagat ggggacttt catgggaagc     960
catcggggtg tttgttgttt gagctatctc atatgttgag gaagaacact aacgagttgt    1020
tgtggctggc ttgtgttttct ttgactgatc agtttgttca tgagaggttg actgatgaaa    1080
gatatcaagc tgcggttatg gagcttgaac aacacatcaa tagctcaggg aatatagata    1140
agatcactag tgttactctg aaagatggaa ccaaggttcg agcaccagac tgttcaagaa    1200
tctcttatga agaagagcct aggcttatgc ttcttagaga gtggacgttg tttgactcca    1260
tgctttgttc ttcatacatt gcgactaagt tgaagacatg gagtgataac ggtatcaaga    1320
aacttaagct tcttctagcg cgtatgggat ttgcacttat cgagtgtcag caaaagtttc    1380
cgtacatgag cctgaggtg aagaggaaga tgaagcaaga gtttgatcgg ttttgccag     1440
aatatgggct taatgatttc tactaccgga gtttcttgcg gcttcatggt tatagctcaa    1500
gggtctctgc tgcagatgtt gtctatggta ttacagcact tcttgaatca tttcttgggt    1560
caggtggctc ctctgcttca aaacagtttg gtgaagctta tgatgctctg tcttgaaca    1620
atttggataa acttcgatct gggatgcaac aagcaatcaa ggttcaacga gcaattctta    1680
gacaaggaag tgcagcaatc actaaaagtg gatgcattcg aagtggtagg aaattcagat    1740
gggtaaagat tgaagattca atggatgcga agtatttggg atatcctcag gccttaacaa    1800
aattctgtta ctttctgatg gatgctttga gagagaaagg agctaggatg aaaccaatgc    1860
tatgtgcctg cgcatctcaa caacctggga agatactcgt ggttgggtt tgtgggaaac    1920
cgaggctcgg ggcagtcaga gggaatgctt ttggcaatgc tttcagaaag gcagctcaag    1980
aaagtagagc tgattacttt cacgagctat tcgagtcttc ttggattgtc ttggatgctt    2040
ctgcagttaa ctcttcatg attagattaa ccgagaagct ctgacatagt ctcattgttc    2100
ttcgattcag tgtgttttct tttatagttt tcagttttat ctcactgttt gcatttttta    2160
cgagcctgtg taataggcac aatctgttat caatcatgta acttgtttaa t             2211
```

<210> SEQ ID NO 7
<211> LENGTH: 978
<212> TYPE: DNA
<213> ORGANISM: Arabidopsis thaliana

<400> SEQUENCE: 7

| | |
|---|---|
| atgcaaatag gtcaagcctt agccgcagca aaggaaggtg agtctcagat gatcgtgatg | 60 |
| atgggtaaca atctttcttt aacaagcatt attctcaatg gagatccatc tatagagcat | 120 |
| aaaggaaaac ttacttgcct tgacgaacaa gtcaagatat ctcagttcta tcactgcgag | 180 |
| ggcttactgc tatgcatttt aaaagatgat tctaggtttg tggtttgtaa tccgtatttg | 240 |
| gagcaaacaa ggtggatcga accaagatat tcccatcgtc catacggaat ggataggttc | 300 |
| tcttacgctc ttggatacgt gaatacggat tcttgtcgta gctacaagtt gttgaggttt | 360 |
| atagattatt actacaatgc acccgagaag caattctttt ggtatgaagt ctacgatttt | 420 |
| gactctgatt tatggactac tcttgatgtc actccacatt ggcgtatagc gttttgtaac | 480 |
| actggcgttc cttttaaggg aaacacttac tggtgtgctg cagaaaggaa cgtagatgta | 540 |
| gatgaagtct tagctaatcg cttaatctgt tttgatttta caaagagaa gcttgcggtt | 600 |
| ttacttcagc acgatgaatc aaatccatat gagcttgact tgtggattac aactaagatt | 660 |
| gagacagaag aggtgttgtg gagcaagttc ttgagagtgg aaacagctgg ttttaatagt | 720 |
| tatgttcctt ttataagtgg aagtttcttc attgacgagg agaagaaagt cgcctttggt | 780 |
| tttgatgaac gtaaccgcca gagagttatt gtcattggag aggctggata cttgaggga | 840 |
| ttggatctcg ttggggattt tggagaccaa agctgtaagc cagatctatg ctcttatgtt | 900 |
| ccaagtttag tgcaaatcaa gcaacctgaa ggaggggaaa gggaagaaga aagcgaatat | 960 |
| ggagaagctt cgatatga | 978 |

<210> SEQ ID NO 8
<211> LENGTH: 1908
<212> TYPE: DNA
<213> ORGANISM: Arabidopsis thaliana

<400> SEQUENCE: 8

| | |
|---|---|
| gtctctcctc tgcatctcct ctgttcctca ggtttctctg ctcatggctg cttatggtca | 60 |
| aatctcctcg ggaatgactg tagatcctca ggttctctct tcctccagaa acattggagt | 120 |
| ttccctatca cctctccgga gaacactaat cggcgccgga gttaggtcta ctagtatctc | 180 |
| tctccgtcaa tgttctctct ccgttagatc gattaaaatc tccgaagata gccgcaaacc | 240 |
| taaagcttat gcagagaacg gtgcttttga tgtgggagtt ttggattctt catcatatag | 300 |
| attggctgat tcaagaacaa gtagtaatga ttcaaggagg aagactaaga ttgtgtgtac | 360 |
| gattggaccg tcttcgagtt ctagggaaat gatttggaaa ctcgcggaag ctggaatgaa | 420 |
| tgtggctcgt tgaatatgt ctcatggtga tcatgcttct catcagataa ctattgattt | 480 |
| agttaaggag tataattctt tgtttgttga caaagctatt gctattatgt tggatacaaa | 540 |
| gggtcctgag gttcgaagcg gggatgtacc gcagccgata tttcttgaag agggtcaaga | 600 |
| gtttaacttt actatcaaga gaggtgtttc gcttaaagac actgttagtg taaattatga | 660 |
| tgattttgtg aacgatgttg aagttgggga tatacttttg gtggatggtg aatgatgtc | 720 |
| gttagctgtt aaatcaaaga cgagtgattt ggtgaagtgt gtggttattg atggtggaga | 780 |
| gcttcaatct agacgtcact tgaatgttcg aggaaagagt gcgactcttc catccattac | 840 |
| agacaaagat tgggaagaca taaaatttgg agtggacaac caagtcgatt tctacgccgt | 900 |

```
ctcctttgtt aaggatgcta aagttgtcca tgagttgaag aactatctca aaacctgcag    960
tgcagacata tcggtgattg tgaaaattga aagtgcagac tctataaaga atcttccttc   1020
tatcatatct gcttgtgatg gggcaatggt tgctcgtgga gatcttggag ctgaacttcc   1080
cattgaagag gtcccgttgt tacaggaaga ataatcaga aggtgtagaa gcattcataa   1140
accagtgatt gttgccacaa acatgctaga gagtatgatt aatcatccaa cgcctacaag   1200
agctgaagtc tctgacattg caattgcagt acgtgaaggc gcagatgcta tcatgctttc   1260
tggtgaaacc gcacatggaa agtttccgct gaaagctgtt aacgtaatgc atactgtggc   1320
gttgagaacc gaggcaagtc tacctgtcag aacctcggca tcccgtacca ctgcttacaa   1380
gggtcacatg gccaaatgt ttgcttttca tgcttctata atggcaaata cactgagctc   1440
accgctaatt gtatttacga gaaccggatc catggcagtg cttctaagcc actaccgccc   1500
atctgcaaca attttcgcct tcacaaacca gagaagaata atgcaaaggc ttgctcttta   1560
tcaaggtgtc atgcctatat atatggagtt ctcggatgat gcagaagata catatgcccg   1620
gtctctcaaa ctcttacagg acgagaatat gctcaaggaa ggacaacatg taactcttgt   1680
ccaaagtggc tcgcaaccca tttggcgtga agaatcaaca catctcatac aagtccgtaa   1740
gataaagata ggtggatgat gttttttactt cttgagctac acaacatctt gcttttactc   1800
agctttcttt ctcttacaca gttcgatcca tatttttttg aatcactcac agtgaatcaa   1860
acaaccatat aaaatttttaa gttattgaag cttttttttct ggttatag             1908

<210> SEQ ID NO 9
<211> LENGTH: 2139
<212> TYPE: DNA
<213> ORGANISM: Arabidopsis thaliana

<400> SEQUENCE: 9
agaaaaaaaa aaaaaaatcc aaattcaaca ctctcacact tcgatatctc cgccttcatt     60
ctcctcagag ccaactgtcc tgagatttcg atttcgattt ctccgatctc tcttcctccg    120
tcgccggcga aaccatgtct cagtctattc aattctccac tccttcacac actcctcacc    180
ttctccatct ccctcactca caattcaacc gtcctctctc ctctatctcc ttccgtcgct    240
tccctctaac aaccatcaaa tacacttcca tcagagcctc ctcgtcatca tctccttcac    300
cggatctcga ttcatcgtcc tcatcatcat cctcgcaagt acttctctca cctaacggta    360
ctggtgctgt gaagtctgat gagagatccg ttgtcgctac ggcggttacg actgatacgt    420
ctgggattga ggttgatact gtgacggaag ctgagcttaa ggagaatgga tttagaagta    480
cgaggaggac gaagctgatc tgtacgatcg gaccggcgac ttgtggattt gagcagcttg    540
aggcgcttgc tgtgggaggt atgaatgtgg caaggcttaa tatgtgtcac ggtacgcgtg    600
attggcaccg cggtgtgatt cgtagtgttc ggaggcttaa tgaggagaaa ggctttgcgg    660
ttgctattat gatggatact gaaggtagtg agattcatat gggagatctt ggtggtgaag    720
cttcagctaa agcagaggat ggtgaggttt ggactttcac tgttagagct tttgattctt    780
ctcgtcctga acgtaccatt agtgttagct acgatggttt cgctgaagat gtaagagttg    840
gggatgaact tttggttgat ggtgggatgg tgagatttga agtgattgag aagattggtc    900
ctgatgttaa gtgtctatgt accgatcctg gattgttgct tcctcgagct aacttgacgt    960
tttggagaga tggaagtctt gtacgagagc gtaatgccat gcttccaaca atttcttcca   1020
aggactggtt ggatattgat tttgaaattg ctgaaggtgt ggattcatt gctgtatcgt   1080 ttgtcaagtc ggctgaagtc attaatcacc ttaaaagtta tcttgctgct cgttcccgtg   1140
```

-continued

| | |
|---|---|
| gaggggaaat tggagtgatt gcaaagatcg agagtatcga ttcactgacc aatttggaag | 1200 |
| aaattattct agcatcagat ggggccatgg ttgcaagagg agatctggga gctcagatac | 1260 |
| ctcttgagca agttccagca gctcaacaga gaatcgtcca agtatgcaga gctcttaaca | 1320 |
| aacccgtcat tgtcgcttca cagctattgg agtccatgat tgagtaccca actccaacca | 1380 |
| gagcagaagt tgccgacgtg tctgaagcag taagacaaag atcagatgca ttgatgctct | 1440 |
| ctggagaatc agctatggga caattcccag acaaggcgct cacggttcta aggactgtca | 1500 |
| gtttaagaat cgagagatgg tggagggaag agaaacgcca tgagtctgta ccgcttcaag | 1560 |
| ccataggctc ttcattttca gacaaaatct cagaagagat ctgtaactca gctgctaaaa | 1620 |
| tggctaacaa tcttggagtg gacgcggttt tcgtttacac aacgagcgga cacatggcat | 1680 |
| cactggtctc ccgatgtcgc ccggactgcc cgatctttgc tttcacaacc acaacctcag | 1740 |
| tgagaagacg cttaaaccta caatggggac ttatcccatt ccgtctcagc ttctcagacg | 1800 |
| acatggaaag caacttgaac aaaacattct cgttactgaa atcaagaggt atgatcaaat | 1860 |
| ctggtgacct cgtgatcgca gtctcggaca tgctgcaatc aatccaggta atgaacgtcc | 1920 |
| cgtaattctc tctctttata caatttcgca atcccgcaaa agagtgtttt gtttcctact | 1980 |
| tttgttactg ttttagact actcttacat tagattccag aggcatcatc atcttcggtt | 2040 |
| tgttaacaac agtaatgtgt aagctttgtt tgtagtgtgt actgtttgtt tttggttttc | 2100 |
| aataatatca gtaatcttat tcaaatattc gattctatc | 2139 |

<210> SEQ ID NO 10
<211> LENGTH: 1491
<212> TYPE: DNA
<213> ORGANISM: Arabidopsis thaliana

<400> SEQUENCE: 10

| | |
|---|---|
| atgggtaaag tagctgttgg agcgactgtt gtttgcacgg cggcggtttg tgcggtggct | 60 |
| gttttggttg ttcgacgacg gatgcagagc tcagggaagt ggggacgtgt tttggctatc | 120 |
| ctcaaggcct ttgaagagga ttgtgcgact ccgatctcga aactgagaca agtggctgat | 180 |
| gctatgaccg ttgagatgca tgctggtctt gcatccgacg tggtagcaa actcaagatg | 240 |
| cttatcagct acgttgataa tcttccttcc ggggatgaaa agggtctctt ttatgcattg | 300 |
| gacctagggg ggacaaactt ccgtgtcatg cgtgtgcttc ttggcgggaa gcaagagcgt | 360 |
| gttgttaaac aagaattcga agaagtttcg attcctcctc atttgatgac tggtggttca | 420 |
| gatgagttgt tcaattttat agctgaagct cttgcgaagt ttgtcgctac agaatgcgaa | 480 |
| gactttcatc ttccagaagg tagacagagg gaattaggtt tcactttctc gtttcctgtt | 540 |
| aagcagactt ctctgtcctc tggtagtctc atcaaatgga caaaggctt ttccatcgaa | 600 |
| gaagcagttg acaagatgt tgttggagca cttaataagg ctctggaaag agttggtctt | 660 |
| gacatgcgaa tcgcagcact tgttaatgat accgttggaa cactagccgg tggtagatac | 720 |
| tataacccgg atgttgttgc tgctgttatt ttaggcactg ggacaaacgc agcctatgtt | 780 |
| gagcgtgcaa ccgcgatccc taatggcat ggtctgcttc caaaatcagg agaaatggtt | 840 |
| ataaacatgg aatggggaaa cttcaggtca tcacatcttc cattaaccga gtttgatcac | 900 |
| acgctggatt tcgagagtct gaatccaggc gaacagattc ttgagaaaat catttccggt | 960 |
| atgtacttgg gagagatttt gcgaagagtt cttctaaaga tggctgaaga tgctgctttc | 1020 |
| tttggcgata cagtcccatc taagctgaga ataccattca tcattaggac tcctcacatg | 1080 |
| tcggctatgc acaacgacac ttctccagac ttgaagattg ttgggagcaa gattaaggat | 1140 |

| | |
|---|---|
| atattggagg tccctacaac ttctctgaaa atgagaaaag ttgtgatcag tctctgcaac | 1200 |
| atcatagcaa cccgaggagc tcgtctctct gctgctggaa tctatggtat tctgaagaaa | 1260 |
| ctgggaagag atactactaa agacgaggag gtgcagaaat cggttatagc catggatggt | 1320 |
| ggattgtttg agcattacac tcagtttagt gagtgtatgg agagctcact aaaagagttg | 1380 |
| cttggagatg aagcttcagg aagcgttgaa gtcactcact ccaatgatgg atcaggcatt | 1440 |
| ggagctgcgc ttcttgctgc ttctcactct ctctaccttg aagactctta a | 1491 |

```
<210> SEQ ID NO 11
<211> LENGTH: 2082
<212> TYPE: DNA
<213> ORGANISM: Arabidopsis thaliana

<400> SEQUENCE: 11
```

| | |
|---|---|
| aagcacttct tctccgcctt cgtaagttcc gccgaaaaga accaaatcct tcactactct | 60 |
| gtctcagctt tcgacctctc tcttctcatt cctttgcaac ttctcacttc tcgaattcct | 120 |
| tctcttcaaa atcagaaatg gctcaagtgg ttgctaccag gtcaattcaa ggctcgatgt | 180 |
| tatctcccaa cggtggatct gtgtctacaa gatccgagaa gctattgaaa ccagcgagtt | 240 |
| ttgcagtgaa ggttcttggc aacgaagcaa agagaagtgg aagagtctct gtaagaagca | 300 |
| gaagagtggt tgatactact gtgagatccg ctcgtgttga gactgaagtc attcctgttt | 360 |
| ctcctgaaga tgtgcctaac agagaggagc agcttgagag gttgttggaa atgcagcagt | 420 |
| tggtgatac atcggtaggg atgtggtcga agccgacagt gaggaggaag acaaagattg | 480 |
| tttgcaccgt tggtccgtcg accaacacac gagaaatgat atggaaattg gctgaagctg | 540 |
| ggatgaatgt tgctaggatg aatatgtctc atggagatca tgcttcacat aagaaggtta | 600 |
| ttgatttggt taaagaatac aatgcacaaa ctaaagacaa cactattgct atcatgcttg | 660 |
| acaccaaggg tccggaagtt aggagtggag atttacctca gccaattatg ttagatcctg | 720 |
| gtcaagagtt taccttttaca attgagagag gagtcagcac accaagttgt gtcagtgtta | 780 |
| actatgatga tttcgttaat gacgtggaag cgggtgacat gcttcttgtt gatggtggta | 840 |
| tgatgtcgtt tatggtgaag tcaaagacca aagactctgt caaatgtgaa gttgttgatg | 900 |
| gtggagaact taagtcaagg agacacctga atgtccgagg aaagagtgca actttacctt | 960 |
| caatcactga gaaggactgg gaggatatta aatttggagt ggagaacaaa gttgactttt | 1020 |
| atgcagtttc ctttgtcaaa gatgctcaag ttgtacacga gttgaagaaa taccttcaaa | 1080 |
| atagtggtgc tgatatacac gtgatagtga aaattgagag tgcagactcc atacctaact | 1140 |
| tgcactccat tatcacagca tcagatgggg caatggttgc aagaggtgat cttggtgcag | 1200 |
| agcttccaat tgaagaagtc cccattcttc aggaggagat cattaacctg tgccgtagta | 1260 |
| tgggaaaagc tgttattgtt gcgactaaca tgcttgagag tatgatagtt catccaactc | 1320 |
| caacccgggc agaggtctca gacattgcta tcgctgttag agaaggtgct gatgcggtaa | 1380 |
| tgctttcagg agaaactgct cacggaaagt tcccattgaa agctgctgga gtgatgcaca | 1440 |
| ctgttgcatt gcgaacagaa gcaaccatta ctagcggtga atgccacct aatcttggtc | 1500 |
| aagccttcaa gaaccatatg agtgagatgt ttgcatacca tgcaaccatg atgtcaaaca | 1560 |
| cacttggaac ttcaactgtt gtcttcacca gaaccggttt catggccata ttgttaagtc | 1620 |
| actatcgtcc ttccggcaca atctatgcct tcacaaatga gaaaaaaata caacaaagat | 1680 |
| tagctttgta tcaaggtgta tgccccatat atatggagtt cacagatgat gcagaagaaa | 1740 |
| cttttgctaa tgctttggct acattactga aacaaggaat ggtgaagaag ggagaggaaa | 1800 |

-continued

```
tagcaatcgt acagagcggt acacagccaa tctggcgatc tcaatcgaca cataacatcc  1860
aagtccgcaa ggtttaaagc ttcttttaag atgggatgtc tttaatatgt agaacctcgt  1920
ttttggttat aattttcgtt gcatgtctct cttctcttgt actattcaca cttgttgttt  1980
gctgtatctt cttcttcagt ttgctttgct acgattgtgg tttttggaga cattatagct  2040
cattaactgt ttgtgagacc aaatgtgtca gaatccgcta tt                     2082
```